United States Patent
Ono

(10) Patent No.: US 8,823,788 B2
(45) Date of Patent: Sep. 2, 2014

(54) IMAGING APPARATUS

(71) Applicant: Olympus Medical Systems Corp., Tokyo (JP)

(72) Inventor: Wataru Ono, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/728,381

(22) Filed: Dec. 27, 2012

(65) Prior Publication Data

US 2013/0222562 A1    Aug. 29, 2013

Related U.S. Application Data

(63) Continuation of application No. PCT/JP2011/078905, filed on Dec. 14, 2011.

(30) Foreign Application Priority Data

Dec. 14, 2010    (JP) .................................. 2010-278350

(51) Int. Cl.
| | | |
|---|---|---|
| A62B 1/04 | (2006.01) | |
| A61B 1/06 | (2006.01) | |
| A61B 1/04 | (2006.01) | |
| A61B 1/05 | (2006.01) | |
| H04N 7/18 | (2006.01) | |
| G02B 23/24 | (2006.01) | |
| H04N 5/235 | (2006.01) | |
| A61B 1/00 | (2006.01) | |
| H04N 13/02 | (2006.01) | |
| H04N 5/225 | (2006.01) | |
| H04N 5/347 | (2011.01) | |

(52) U.S. Cl.
CPC *H04N 7/18* (2013.01); *A61B 1/042* (2013.01); *A61B 1/0638* (2013.01); *A61B 1/05* (2013.01); *H04N 2005/2255* (2013.01); *H04N 5/347* (2013.01); *G02B 23/2423* (2013.01); *A61B 1/043* (2013.01); *H04N 5/2354* (2013.01); *A61B 1/00186* (2013.01); *A61B 1/00163* (2013.01); *A61B 1/00124* (2013.01); *H04N 13/02* (2013.01); *A61B 1/00128* (2013.01); *A61B 1/00126* (2013.01); *H04N 5/2256* (2013.01)
USPC ............................................. 348/65; 600/180

(58) Field of Classification Search
CPC .. A61B 1/0638; A61B 1/00186; A61B 1/043; A61B 1/042
USPC ............................................. 348/65; 600/180
See application file for complete search history.

(56) References Cited

U.S. PATENT DOCUMENTS

2007/0007436 A1* 1/2007 Maksymowicz ............ 250/208.2
2007/0046778 A1* 3/2007 Ishihara et al. ................ 348/68
2011/0158530 A1* 6/2011 Okihara et al. .............. 382/173

FOREIGN PATENT DOCUMENTS

JP    2001-221961    8/2001
(Continued)

OTHER PUBLICATIONS

Partial English Language Translation of Japanese Patent Laid-Open Publication No. JP 2006-288821 A published Oct. 26, 2006.

(Continued)

*Primary Examiner* — Sath V Perungavoor
*Assistant Examiner* — Xiaolan Xu
(74) *Attorney, Agent, or Firm* — Scully, Scott, Murphy & Presser, P.C.

(57) ABSTRACT

An imaging apparatus includes: a first and second optical systems that focus and emit incident light, a transparent wavelength, and a focal length of them being different from each other; an imaging unit that includes a first region on which the light emitted from the first optical system is incident and a second region on which the light emitted from the second optical system is incident, can output, as pixel information, an electric signal after photoelectric conversion from pixels arbitrarily set as read targets; a setting unit that can arbitrarily set the read targets in at least one of the first region and the second region; a reading unit that reads the pixel information from the read targets; a control unit that changes the read targets according to an acquisition target image; and an image processing unit that generates the acquisition target image.

17 Claims, 29 Drawing Sheets

(56) References Cited

FOREIGN PATENT DOCUMENTS

| JP | 2002-336196 A | 11/2002 |
|----|---------------|---------|
| JP | 2003-005096   | 1/2003  |
| JP | 2003-333432   | 11/2003 |
| JP | 2006-288821   | 10/2006 |
| JP | 2006-325973   | 12/2006 |
| JP | 2007-090044   | 4/2007  |
| JP | 2009-34224 A  | 2/2009  |

OTHER PUBLICATIONS

Partial English Language Translation of Japanese Patent Laid-Open Publication No. JP 2003-005096 A published Jan. 8, 2003.

International Search Report dated Jan. 24, 2012 issued in PCT/JP2011/078905.

\* cited by examiner

| OBSERVATION IMAGE | READING REGION | GAIN ADJUSTMENT |
|---|---|---|
| POLARIZED IMAGE | REGION S1 | TWO TIMES |
| UNPOLARIZED IMAGE | REGION S2 | ONE TIME |

| OBSERVATION IMAGE | ILLUMINATION | READING REGION | EXPOSURE TIME | GAIN ADJUSTMENT | BINNING OUTPUT |
|---|---|---|---|---|---|
| FLUORESCENCE OBSERVATION IMAGE | SPECIAL LIGHT | REGION S21 | LONG | HIGH | PRESENT |
| NORMAL IMAGE | WHITE LIGHT | REGION S22 | STANDARD | STANDARD | ABSENT |

| OBSERVATION IMAGE | ILLUMINATION | READING REGION (ACQUIRED IMAGE) | | EXPOSURE TIME | GAIN ADJUSTMENT | | IMAGE PROCESSING |
|---|---|---|---|---|---|---|---|
| NORMAL OBSERVATION IMAGE | WHITE LIGHT | REGION S31 | ALL PIXELS (R+G) | STANDARD | REGION S31 | STANDARD | COMPOSITION (GENERATE NORMAL OBSERVATION IMAGE) |
| | | REGION S32 | ALL PIXELS (B) | | REGION S32 | STANDARD | |
| NBI OBSERVATION IMAGE | NBI ILLUMINATION LIGHT | REGION S31 | PIXELS OTHER THAN R PIXEL (G) | LONG | REGION S31 | HIGH | COMPOSITION (GENERATE NBI OBSERVATION IMAGE) |
| | | REGION S32 | ALL PIXELS (B) | | REGION S32 | HIGH | |
| FLUORESCENCE OBSERVATION IMAGE | EXCITATION LIGHT | REGION S31 | ALL PIXELS (R+G) | LONG | REGION S31 | HIGH | GENERATE FLUORESCENCE OBSERVATION IMAGE |
| | | REGION S32 | NO READ (-) | | REGION S32 | - | |

T3

IMAGING APPARATUS

CROSS-REFERENCES TO RELATED APPLICATIONS

This application is a continuation of PCT international application Ser. No. PCT/JP2011/078905 filed on Dec. 14, 2011 which designates the United States, incorporated herein by reference, and which claims the benefit of priority from Japanese Patent Applications No. 2010-278350, filed on Dec. 14, 2010, incorporated herein by reference.

BACKGROUND OF THE INVENTION

1. Field of the Invention

The present invention relates to an imaging apparatus including an imaging unit that can output, as pixel information, an electric signal after photoelectric conversion from pixels which are arbitrarily set as read targets among a plurality of pixels for imaging.

2. Description of the Related Art

Conventionally, in the field of medicine, an endoscope system is used to observe internal organs of a subject. In the endoscope system, in general, an elongated flexible insertion portion is inserted into a body cavity of the subject, such as a patient, white light is emitted to body tissues in the body cavity through the insertion portion, and an imaging unit provided at a distal end of the insertion portion receives light reflected from the body tissues and forms an in-vivo image. As such, the captured body image is displayed on a monitor of the endoscope system. The user, such as a doctor, observes the body cavity of the subject using the in-vivo image displayed on the monitor of the endoscope system.

An endoscope system has been achieved, which can acquire images different from a normal image such as a fluorescence observation image along with a normal image formed by white light. As the endoscope system, for example, Japanese Patent Application Laid-open No. 2009-034224 discloses a structure in which an imaging element for acquiring a normal image and an imaging element for acquiring another image are provided in a tip portion of an endoscope. In addition, for example, Japanese Patent Application Laid-open No. 2002-336196 discloses a structure in which a switching mechanism or an adjustment mechanism is provided for each imaging optical system and each filter and one imaging element is used to acquire a normal image and another image.

SUMMARY OF THE INVENTION

An imaging apparatus according to one aspect of the present invention includes: a first optical system that focuses incident light and emits the focused light; a second optical system that focuses incident light, emits the focused light, and is different from the first optical system in at least one of polarization characteristics, a transparent wavelength, and a focal length; an imaging unit that includes a first region on which the light emitted from the first optical system is incident and a second region which is different from the first region and on which the light emitted from the second optical system is incident, can output, as pixel information, an electric signal after photoelectric conversion from pixels which are arbitrarily set as read targets among a plurality of pixels for imaging; a setting unit that can arbitrarily set pixels as the read targets in the imaging unit and sets the pixels in at least one of the first region and the second region as the read targets; a reading unit that reads the pixel information from the pixels which are set as the read targets by the setting unit among the plurality of pixels for imaging in the imaging unit; a control unit that changes the pixels set as the read targets by the setting unit according to an acquisition target image; and an image processing unit that generates the acquisition target image in accordance with at least one of the pixel information items of the pixels read by the reading unit.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 22 is a diagram illustrating an example of a control condition list table stored in a control condition memory illustrated in FIGS. 18A and 18B;

DETAILED DESCRIPTION OF THE PREFERRED EMBODIMENTS

Figure 1:
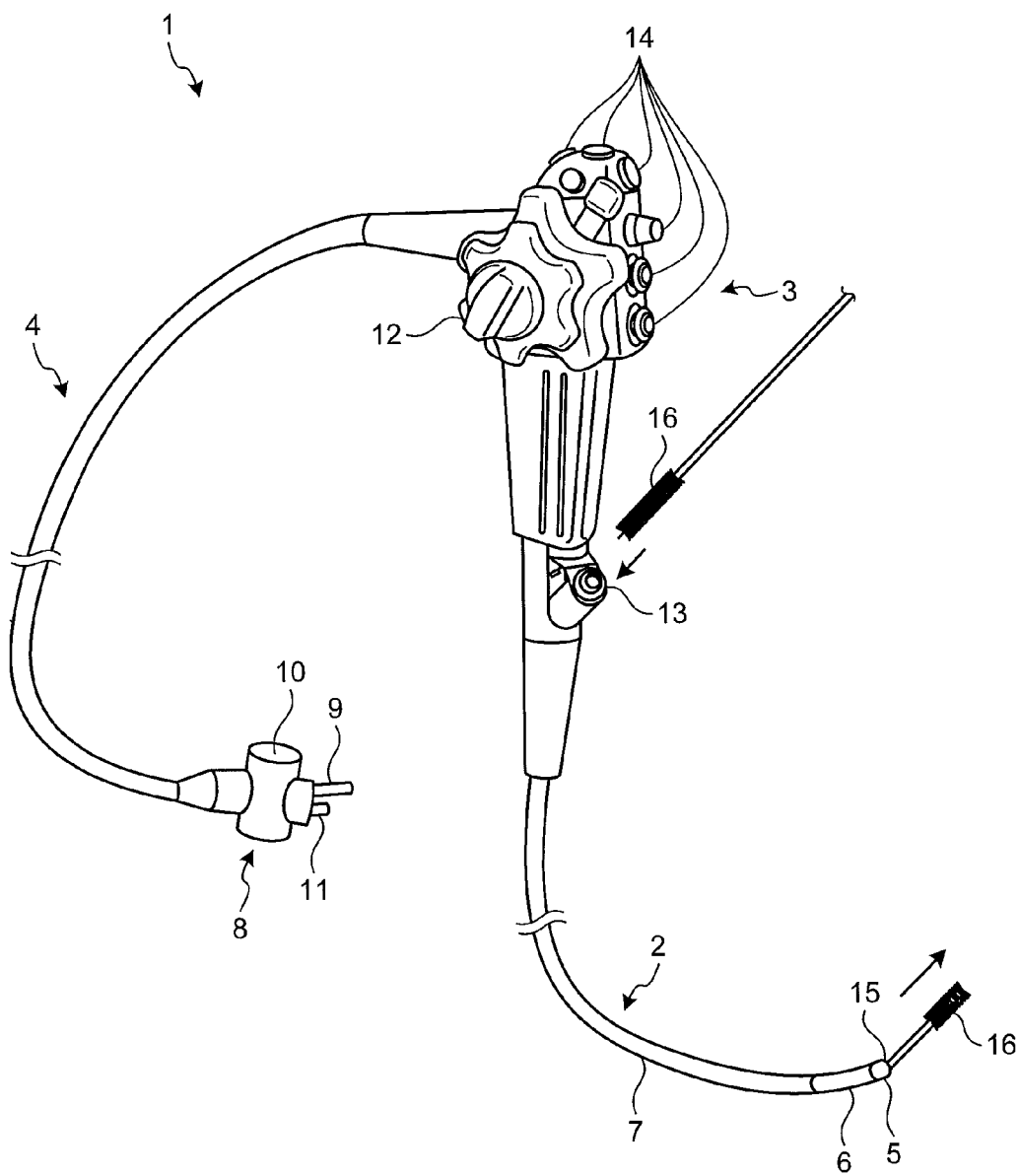
FIG. 1 is a diagram illustrating the schematic structure of an endoscopic portion according to a first embodiment.

Hereinafter, a medical endoscope system according to an embodiment of the invention which includes an imaging element at a distal end of an insertion portion, captures an image of a body cavity of a subject, such as a patient, and displays the captured image will be described. The invention is not limited by this embodiment. In the drawings, the same components are denoted by the same reference numerals. In addition, the drawings are illustrative and it is noted that, for example, the relation between the thickness and the width of each member and the scale of each member are different from the actual dimensions and scale. In the drawings, the relation between dimensions and the scales may be different.

First Embodiment

First, an endoscope system according to a first embodiment will be described. FIG. 1 is a diagram illustrating a schematic structure of an endoscopic portion of the endoscope system according to the first embodiment. As illustrated in FIG. 1, an endoscope 1 according to the first embodiment includes an elongated insertion portion 2, an operation unit 3 that is disposed at a proximal end of the insertion portion 2 and is held by an operator of the endoscope, and a flexible universal code 4 that extends from a side of the operation unit 3. The universal code 4 includes a light guide cable, an electric cable, or the like.

The insertion portion 2 includes a tip portion 5 having a CMOS sensor as an imaging element provided therein, a curved portion 6 that includes a plurality of curved pieces and can be curved, and a long flexible tube portion 7 that is provided at a proximal end of the curved portion 6 and is long and flexible.

A connector portion 8 is provided at an end of the universal code 4. The connector portion 8 is provided with a light guide connector 9 that is connected to a light source device such that it can be disconnected therefrom, an electric contact portion 10 that is connected to a control device in order to transmit an electric signal of an object image which is converted from an optical signal by the CMOS sensor to a control device for signal processing, and an air feeding cap 11 for sending air to a nozzle of the tip portion 5. The light source device includes, for example, a white light source or a special light source and supplies light emitted from the white light source or the special light source as illumination light to the endoscope 1 which is connected through the light guide connector 9. The control device supplies power to the imaging element and receives the electric signal which is converted from an optical signal by the imaging element. The control device processes the electric signal of the image captured by the imaging element and displays the image on the connected display unit. In addition, the control device controls, for example, a gain adjustment of the imaging element and outputs a driving signal for driving the imaging element.

The operation unit 3 includes a bending knob 12 that bends the curved portion 6 in a vertical direction and a horizontal direction, a treatment tool insertion portion 13 that inserts a treatment tool 16, such as a biopsy forceps or a laser probe, into the body cavity, and a plurality of switches 14 that are used to operate the control device, the light source device, or peripheral devices, such as an air supply unit, a water supply unit, and a gas supply unit. The treatment tool 16 which is inserted from the treatment tool insertion portion 13 gets out of an opening portion 15 provided at the distal end of the insertion portion 2 through a treatment tool channel which is provided in the treatment tool 16. For example, when the treatment tool 16 is a biopsy forceps, for example, biopsy, such as the collection of an affected tissue, is performed by the biopsy forceps.

Figure 2:
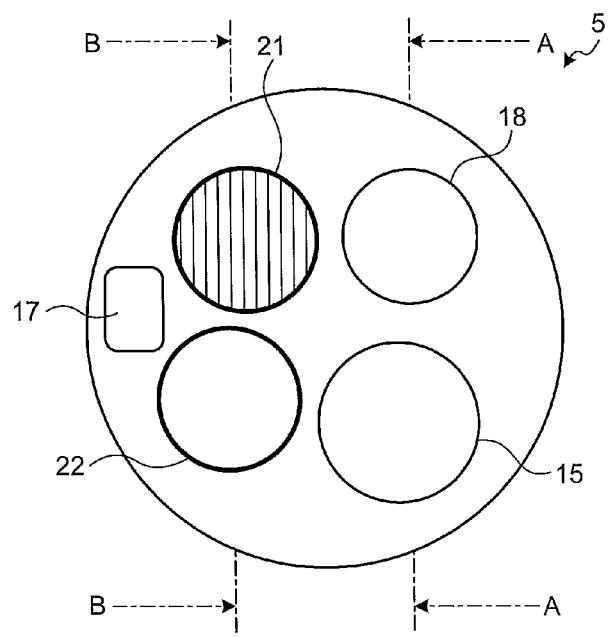
FIG. 2 is a diagram illustrating a distal end surface of a tip portion of the endoscope illustrated in FIG. 1.
Figure 3:
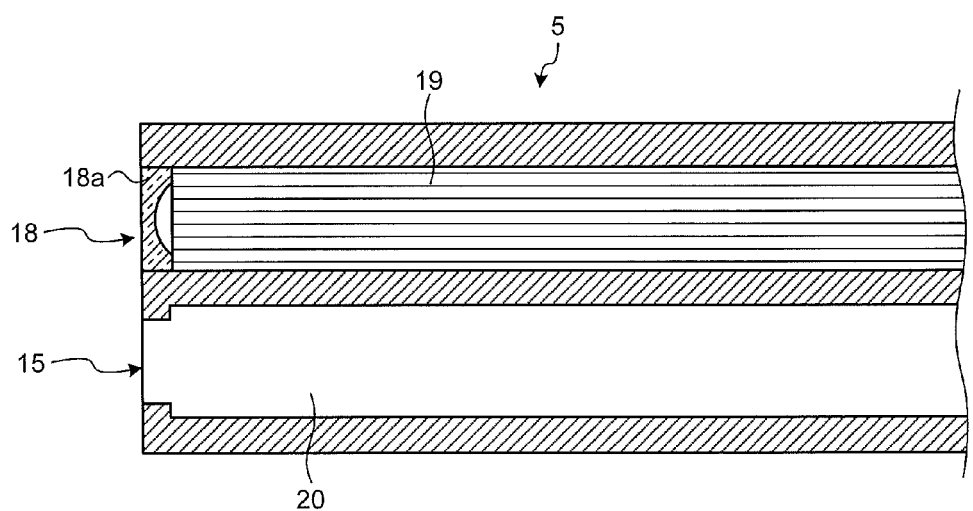
FIG. 3 is a diagram illustrating a portion of a cross-section of the tip portion taken along the line A-A of FIG. 2.
Figure 4:
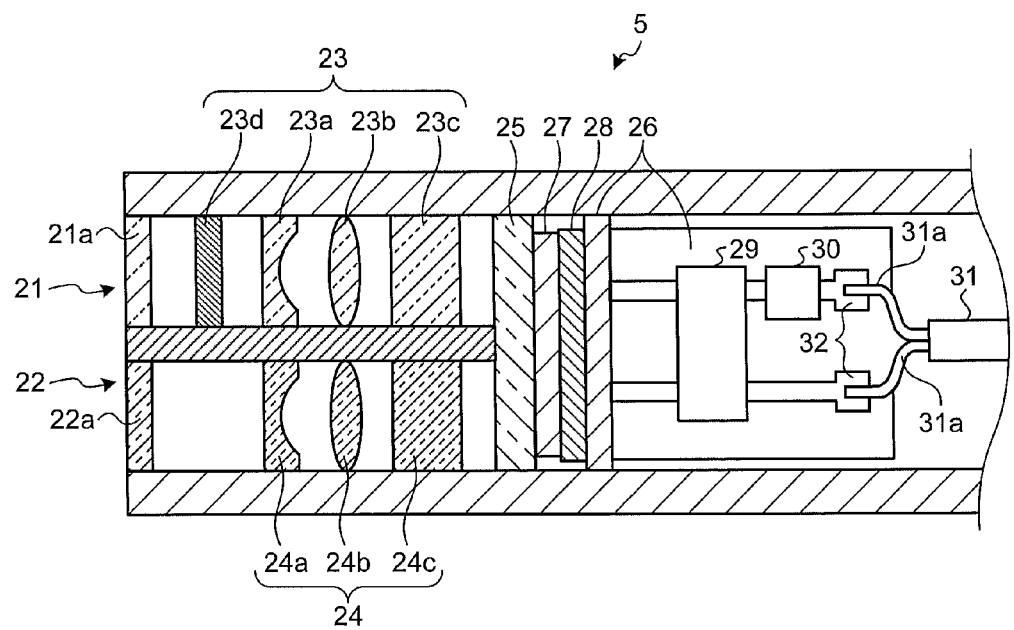
FIG. 4 is a diagram illustrating a portion of a cross-section of the tip portion taken along the line B-B of FIG. 2.

Next, the structure of the tip portion 5 of the insertion portion 2 will be described. FIG. 2 is a diagram illustrating the distal end surface of the tip portion 5 of the endoscope 1 illustrated in FIG. 1. FIG. 3 is a diagram illustrating a portion of a cross-section of the tip portion 5 taken along the line A-A of FIG. 2. FIG. 4 is a diagram illustrating a portion of a cross-section of the tip portion 5 taken along the line B-B of FIG. 2.

As illustrated in FIG. 2, the opening portion 15 for presenting a treatment tool, a cleaning nozzle 17, an illumination window 18 from which illumination light is emitted, an observation window 21, and an observation window 22 are provided in the distal end surface of the tip portion 5 of the endoscope 1 illustrated in FIG. 1.

As illustrated in FIG. 3, in the illumination window 18, white light or special light which is supplied from the light source device through a light guide 19 including such as a bundle of glass fibers is emitted from an illumination lens 18a. The opening portion 15 for presenting a treatment tool communicates with a treatment tool channel 20.

As illustrated in FIG. 4, the observation window 21 and the observation window 22 are blocked by cover glasses 21a and 22a, respectively. Light which is incident through the observation window 21 from the outside is incident on a first optical system 23 and is focused. Light which is incident through the observation window 22 from the outside is incident on a second optical system 24 different from the first optical system 23 and is focused.

Figure 5:
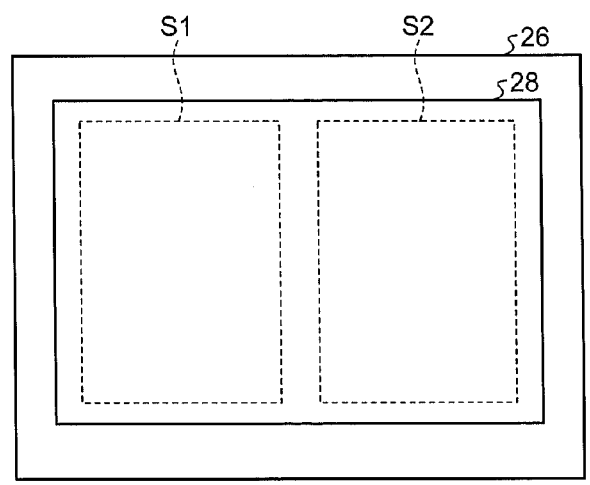
FIG. 5 is a diagram illustrating an example of a light receiving region provided in a light receiving unit illustrated in FIG. 3.

A light receiving unit 28 includes a plurality of pixels for imaging which are two-dimensionally arranged in a matrix and is arranged so as to receive both light emitted from the first optical system 23 and light emitted from the second optical system 24. The light receiving unit 28 receives light which is incident through the first optical system 23 and the second optical system 24, respectively and captures the image of the body cavity. As illustrated in FIG. 5, the light receiving unit 28 includes a light receiving surface including a region S1 on which the light emitted from the first optical system 23 is incident and a region S2 which is different from the region S1 and on which the light emitted from the second optical system 24 is incident.

A cover glass 25 is provided on the light receiving surface side of the light receiving unit 28. An on-chip filter 27 in which an R, G, or B filter corresponding to the array of the pixels of the light receiving unit 28 is arranged is provided between the cover glass 25 and the light receiving unit 28. The light receiving unit 28, a driver 29 that instructs the imaging time of the light receiving unit 28 and simultaneously supplies power, and a conversion circuit 30 that reads the image signal obtained by the light receiving unit 28 and converts the image signal into an electric signal are mounted on a circuit board 26. A plurality of electrodes 32 are provided on the circuit board 26. The electrodes 32 are connected to signal lines 31a which transmit electric signals between the control devices through, for example, an anisotropically-conductive resin film. An assembled cable 31 is formed by a plurality of signal lines 31a such as a signal line that transmits an image signal, which is an electric signal output from the light receiving unit 28, or a signal line that transmits a control signal from the control device.

The first optical system 23 includes lenses 23a to 23c and a light detecting member 23d that is provided close to the observation window, detects only a component which is polarized along a first polarization plane among incident light components, and transmits the detected component. Therefore, the first optical system 23 emits only the component which is polarized along the first polarization plane among the light components incident through the observation window 21 to the region S1 of the light receiving unit 28. The second optical system 24 includes lenses 24a to 24c and transmits light incident through the observation window 22 to the region S2 of the light receiving unit 28 as it is. The region S1 and the region S2 are different from each other.

In the endoscope system according to the first embodiment, a CMOS sensor 80 which can read information only from a pixel with an arbitrary set address among the pixels of the light receiving unit 28 is used as the imaging element. In the endoscope system according to the first embodiment, a read address setting unit 53 sets a read target pixel according to the image to be acquired. In the first embodiment, pixel information is read from each of the pixels in the region S1 of the light receiving unit 28 corresponding to the first optical system 23 which emits only the component polarized along the first polarization plane and the pixels in the region S2 of the light receiving unit 28 corresponding to the second optical system 24 that emits unpolarized light. Therefore, a polarized image obtained by the component polarized along a predetermined plane and a normal image obtained by unpolarized light are acquired as an observation image at the same time.

Figure 6A:
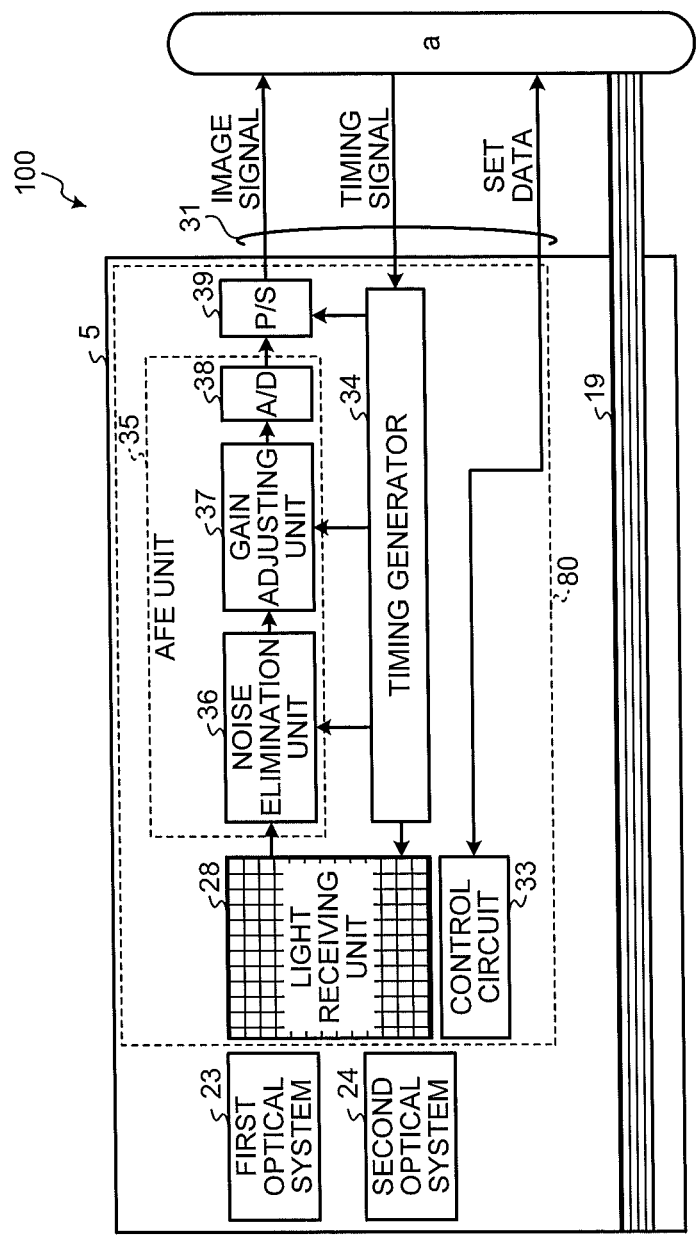
FIGS. 6A and 6B are block diagrams illustrating the structure of an endoscope system according to the first embodiment.
Figure 6B:
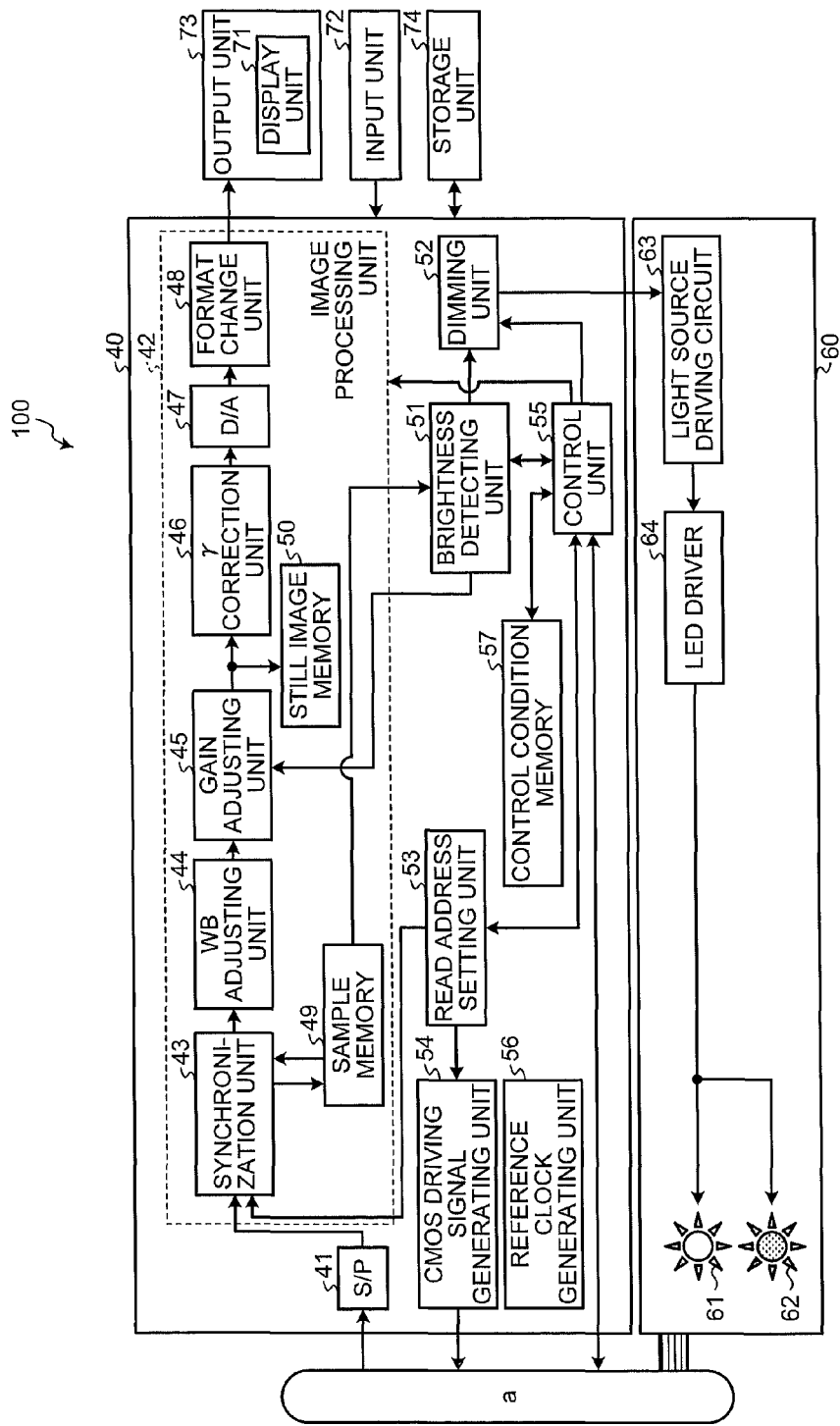

Next, the structure of the endoscope system according to the first embodiment will be described in detail. FIGS. 6A and 6B are block diagrams illustrating the structure of the endoscope system according to the first embodiment. As illustrated in FIGS. 6A and 6B, an endoscope system 100 according to the first embodiment includes a control device 40 that is connected to the CMOS imaging element 80 provided in the tip portion 5 through the assembled cable 31 including a plurality of signal lines, a light source device 60 that supplies white light or special light, an output unit 73 that outputs information about in-vivo observation and includes a display unit 71 that displays an in-vivo image captured by the CMOS imaging element 80, an input unit 72 that inputs various kinds of instruction information required for in-vivo observation, and a storage unit 74 that stores, for example, an in-vivo image.

The first optical system 23, the second optical system 24, and the CMOS imaging element 80 are provided in the tip portion 5. The CMOS imaging element 80 includes the light receiving unit 28, a control circuit 33, a timing generator 34, an AFE (Analog Front End) unit 35 including a noise elimination unit 36, a gain adjusting unit 37, and an A/D conversion unit 38, and a P/S conversion unit 39 that converts an input digital signal from a parallel signal into a serial signal. The light receiving unit 28 and CMOS sensor peripheral circuits forming the CMOS imaging element 80 are, for example, integrated into one chip.

The light receiving unit 28 outputs an electric signal which is converted from an optical signal as pixel information from an arbitrary set pixel designated as a read target among the plurality of pixels for imaging which are two-dimensionally arranged in a matrix. Each pixel information item includes a brightness value. The light receiving unit 28 functions as an imaging unit in the claims.

The control circuit 33 controls the imaging process of the light receiving unit 28, the imaging speed of the light receiving unit 28, a process of reading the pixel information from the pixels of the light receiving unit 28, and a process of transmitting the read pixel information, in accordance with set data which is output from the control device 40.

The timing generator 34 is driven according to a timing signal output from the control device 40 and outputs, as the pixel information, an electric signal which is converted from an optical signal from a pixel which is disposed at the position (address) designated as a read target among the plurality of pixels forming the light receiving unit 28 in the reading order set by the read address setting unit 53.

The noise elimination unit 36 eliminates noise in the signal of the pixel information which is output from a predetermined pixel of the light receiving unit 28. The gain adjusting unit 37 amplifies the brightness value of the pixel information output from the noise elimination unit 36 at a gain indicated in the set data output from a control unit 55, and then outputs the amplified value to the A/D conversion unit 38. The A/D conversion unit 38 converts the signal of the pixel information from which noise has been eliminated from an analog signal into a digital signal and outputs the digital signal to the P/S conversion unit 39. The P/S conversion unit 39 converts the pixel information which is read from the light receiving unit 28 by the timing generator 34 and the AFE unit 35 into a serial image signal, and then the serial image signal is transmitted to the control device 40 through a predetermined signal line of the assembled cable 31. The timing generator 34 and the AFE unit 35 function as a reading unit in the claims.

The control device 40 processes the image signal, displays an in-vivo image on the display unit 71, and controls each component of the endoscope system 100. The control device 40 includes an S/P conversion unit 41, an image processing unit 42, a brightness detecting unit 51, a dimming unit 52, the read address setting unit 53, a CMOS driving signal generating unit 54, the control unit 55, a reference clock generating unit 56, and a control condition memory 57.

The S/P conversion unit 41 converts an image signal, which is a digital signal received from the tip portion 5, from a serial signal into a parallel signal.

The image processing unit 42 generates an in-vivo image, which will be displayed on the display unit 71 in accordance with the address of the pixel of the light receiving unit 28 read by the timing generator 34 and the AFE unit 35, from the parallel image signal output from the S/P conversion unit 41, that is, the pixel information of the pixel read by the timing generator 34 and the AFE unit 35.

The image processing unit 42 includes a synchronization unit 43, a WB adjusting unit 44, a gain adjusting unit 45, a γ correction unit 46, a D/A conversion unit 47, a format change unit 48, a sample memory 49, and a still image memory 50.

The synchronization unit 43 inputs the input image signals of R, G, and B pixels to memories (not illustrated) which are provided for each pixel, stores each memory value so as to correspond to the addresses of the pixels of the light receiving unit 28 read by the timing generator 34 and the AFE unit 35 while sequentially updating the memory values with each input image signal, and synchronizes the image signals of three memories as R, G, and B image signals. The synchronized R, G, and B image signals are sequentially output to the WB adjusting unit 44. In addition, some of the synchronized R, G, and B image signals are also output to the sample memory 49 for image analysis, such as brightness detection, and are then stored therein.

The WB adjusting unit 44 adjusts the white balance of the R, G, and B image signals. The gain adjusting unit 45 adjusts the gain of the R, G, and B image signals. The γ correction unit 46 performs grayscale conversion on the R, G, and B image signals so as to correspond to the display unit 71.

The D/A conversion unit 47 converts the grayscale-converted R, G, and B image signals from digital signals into analog signals. The format change unit 48 changes the format of the image signal converted into the analog signal to a hi-vision format and the like and outputs the signal to the display unit 71. As a result, one in-vivo image is displayed on the display unit 71. Some of the R, G, and B image signals whose gain has been adjusted by the gain adjusting unit 45 are stored as an image signal for still image display, an image signal for enlarged image display, and an image signal for emphasized image display in the still image memory 50.

The brightness detecting unit 51 detects a brightness level corresponding to each pixel from the R, G, and B image signals stored in the sample memory 49 and stores the detected brightness level in a memory which is provided in the brightness detecting unit 51. In addition, the brightness detecting unit 51 calculates a gain adjustment value and the amount of light emitted, in accordance with the detected brightness level. The calculated gain adjustment value is output to the gain adjusting unit 45 and the calculated amount of light emitted is output to the dimming unit 52. The detection result obtained by the brightness detecting unit 51 is also output to the control unit 55.

The dimming unit 52 sets the amount of current supplied to each light source and the driving conditions of a dimming filter in accordance with the amount of light emitted which is output from the brightness detecting unit 51 under the control of the control unit 55, and outputs a light source synchronous signal including the set conditions to the light source device 60. The dimming unit 52 sets the kind of light emitted from the light source device 60, the amount of light emitted from the light source device 60, and a light emission time.

The read address setting unit 53 can arbitrarily set the read target pixels of the light receiving unit 28 and the order in which the pixels are read. That is, the read address setting unit 53 can arbitrarily set the addresses of the pixels of the light receiving unit 28 which are read by the timing generator 34 and the AFE unit 35. In addition, the read address setting unit 53 outputs the set addresses of the read target pixels to the synchronization unit 43.

The CMOS driving signal generating unit 54 generates a driving timing signal for driving the light receiving unit 28 and the CMOS sensor peripheral circuits and outputs the generated driving timing signal to the timing generator 34 through predetermined signal lines in the assembled cable 31. The timing signal includes the address of the read target pixel.

The control unit 55 includes, for example, a CPU, reads various programs stored in a memory (not illustrated), and performs various processes indicated by the programs, thereby controlling the driving of each unit and the input and output of information to and from each unit and processing various kinds of information between the units. The control device 40 outputs set data for imaging control to the control circuit 33 provided in the tip portion 5 through a predetermined signal line of the assembled cable 31. The set data includes, for example, the imaging speed of the light receiving unit 28, instruction information for instructing the reading speed of pixel information from an arbitrary pixel of the light receiving unit 28, and instruction information indicating the gain of the brightness value of the read pixel information, and transmission control information for the read pixel information.

The control unit 55 changes the read target pixel and the reading order set by the read address setting unit 53. The control unit 55 changes the read target pixel and the reading order set by the read address setting unit 53 according to the image to be acquired. The control unit 55 controls the read target pixel setting process of the read address setting unit 53, the reading process of the timing generator 34 and the AFE unit 35, and the image generating process of the image processing unit 42 in correspondence with the image to be acquired.

The control condition memory 57 stores the control conditions of the control unit 55 so as to correspond to the image to be acquired. The control unit 55 controls the read target pixel setting process of the read address setting unit 53, the reading process of the timing generator 34 and the AFE unit 35, and the image generating process of the image processing unit 42, in accordance with the control condition corresponding to the image to be acquired among the control conditions stored in the control condition memory 57.

The reference clock generating unit 56 generates a reference clock signal, which is a standard for the operation of each unit of the endoscope system 100, and supplies the generated reference clock signal to each unit of the endoscope system 100.

The light source device 60 performs a light emission process under the control of the control unit 55. The light source device 60 includes a white light source 61 which is, for example, an LED and emits white illumination light, a special light source 62 that emits, as special light, any one of R, G, and B light components which are in a wavelength band different from that of the white illumination light and whose band is narrowed by a narrow bandpass filter, a light source driving circuit 63 that controls the amount of current supplied to the white light source 61 or the special light source 62 or the driving of the dimming filter in accordance with the light source synchronous signal transmitted from the dimming unit 52, and an LED driver 64 that supplies a predetermined amount of current to the white light source 61 or the special light source 62 under the control of the light source driving circuit 63. Light emitted from the white light source 61 or the special light source 62 is supplied to the insertion portion 2 through the light guide 19 and is then emitted from the distal end of the tip portion 5 to the outside.

In the first embodiment, the polarized image and the normal image are acquisition target images. The control unit 55 controls each unit in accordance with, for example, the control condition indicated in a table T1 illustrated in FIG. 7 among the control conditions stored in the control condition memory 57. In this way, the endoscope system 100 acquires both the polarized image and the normal image as observation images at the same time.

Specifically, as illustrated in a table T1, the control unit 55 changes the pixels for a polarized image in the region S1 of the light receiving unit 28 corresponding to the first optical system 23 which emits only the component polarized along the predetermined first polarization plane and the pixels for an unpolarized image in the region S2 of the light receiving unit 28 corresponding to the second optical system which emits unpolarized light to the read target pixels set by the read address setting unit 53. Therefore, the read address setting unit 53 sets both the pixels in the region S1 corresponding to the polarized image and the pixels in the region S2 corresponding to the unpolarized image among the pixels of the light receiving unit 28 as the read target pixels, under the control of the control unit 55. Then, the timing generator 34 and the AFE unit 35 read pixel information from the pixels in the region S1 and the pixels in the region S2 which are set as the read target pixels by the read address setting unit 53 among the plurality of pixels for imaging in the light receiving unit 28. The timing generator 34 and the AFE unit 35 do not read the pixel information from the pixels other than the pixels in the regions S1 and S2 of the light receiving unit 28.

The control unit 55 directs the image processing unit 42 to generate two images in accordance with the pixel information which is read from the pixels in the regions S1 and S2 by the timing generator 34 and the AFE unit 35. The image processing unit 42 generates a polarized image in accordance with the pixel information from the pixels in the region S1 and generates an unpolarized image in accordance with the pixel information of the second region. The display unit 71 displays two images, that is, the polarized image and the unpolarized image generated by the image processing unit 42 at the same time.

As such, in the first embodiment, the first optical system 23 and the second optical system 24 are provided according to the polarized image and the unpolarized image, which are acquisition targets, and different reading regions are set as reading regions corresponding to the first optical system 23 for a polarized image and the second optical system 24 for an unpolarized image in the light receiving unit 28. In the first embodiment, the pixel information is read from the pixels in each region. In this way, the pixel information which is a source of the polarized image and the pixel information which is a source of the unpolarized image are acquired at the same time, without performing a trimming process. Therefore, according to the first embodiment, it is possible to effectively acquire plural kinds of images with a simple structure including one CMOS imaging element 80. In the first embodiment, a switching mechanism, an adjustment mechanism, or a plurality of light receiving units may not be provided in the optical system and it is possible to reduce the number of peripheral circuits of the imaging element or the number of wiring lines. Therefore, it is possible to reduce the diameter of the tip portion 5 of the endoscope 1.

In the first embodiment, the read target pixels are set for each acquisition target image so as to correspond to the acquisition target images and the gain of the amplification process performed by the gain adjusting unit 37 of the AFE unit 35 is changed to acquire an appropriate polarized image and an appropriate unpolarized image. The first optical system 23 emits only the component which is polarized along the first polarization plane among the light components incident from the outside to the first region of the light receiving unit 28. Therefore, the amount of light received in the region S1 is less than that of light received in the region S2 on which light is incident from the outside by the second optical system 24, without being polarized.

The control unit 55 directs the gain adjusting unit 37 to amplify the brightness value of the pixel in the region S1 at a gain more than that at which the brightness value of the pixel in the region S2 is amplified and output the amplified value. For example, as illustrated in the table T1 of FIG. 7, the control unit 55 sets the gain adjustment conditions of the CMOS imaging element 80 such that the gain remains 1 in the region S2 on which unpolarized light is incident and the gain is 2 in the region S1 on which the component polarized by the first polarization plane is incident. As a result, the gain adjusting unit 37 amplifies the brightness value of the pixel in the region S1 in which the amount of light received is less than that in the region S2 at a gain more than that for the region S2 and outputs the amplified brightness value to the control device 40.

As such, the gain adjusting unit 37 amplifies the brightness value in the pixel information at different gains for each region and the CMOS imaging element 80 outputs the pixel information with an appropriate brightness value. In this way, it is possible to generate an unpolarized image with appropriate brightness, without adjusting the gain with the image processing unit 42 of the control device 40. Therefore, it is possible to effectively perform the image generating process.

In the first embodiment, both the polarized image and the unpolarized image are displayed at the same time. However, the display of the polarized image and the display of the unpolarized image may be switched. In this case, in the first embodiment, the control unit 55 may switch the images displayed on the display unit 71 in accordance with display image selection information which is input from the input unit 72 to the control device 40. In addition, in the first embodiment, display images may be switched in real time since the pixel information items corresponding to both the polarized image and the unpolarized image are read at the same time. When the polarized image and the unpolarized image with the same resolution are acquired, the regions S1 and S2 of the light receiving unit 28 may have the same area and shape in order to equalize the number of pixels.

First Modification of First Embodiment

Figures 7, 8:
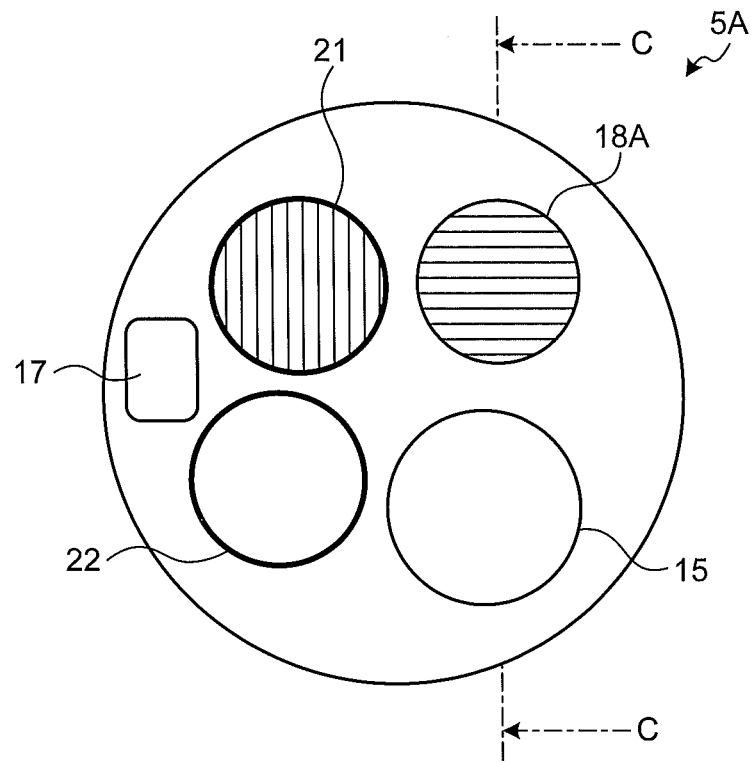
FIG. 7 is a diagram illustrating an example of a control condition list table stored in a control condition memory illustrated in FIGS. 6A and 6B.
FIG. 8 is a diagram illustrating an example of a distal end surface of a tip portion of an endoscope according to a first modification of the first embodiment.
Figure 9:
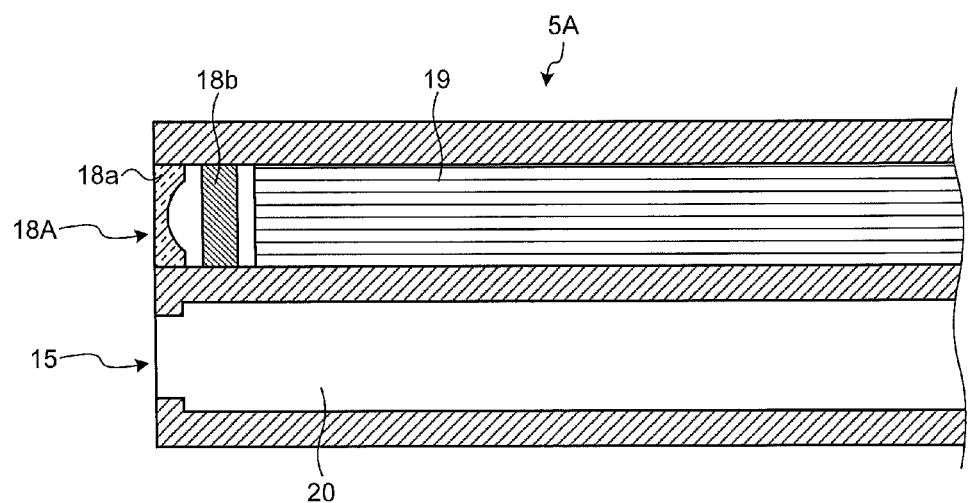
FIG. 9 is a diagram illustrating a portion of a cross-section of the tip portion taken along the line C-C of FIG. 8.

Next, a first modification of the first embodiment will be described. FIG. 8 is a diagram illustrating an example of the distal end surface of a tip portion of an endoscope according to the first modification of the first embodiment. FIG. 9 is a diagram illustrating a portion of the cross-section of a tip portion 5A taken along the line C-C of FIG. 8.

As illustrated in FIGS. 8 and 9, in the first modification of the first embodiment, a light detecting member 18b which transmits only the component polarized along a second polarization plane perpendicular to the first polarization plane by the light detecting member 23d of the first optical system 23 is provided between the light guide 19 and the illumination lens 18a, among incident light components. In this way, among light components emitted from the white light source 61, the component which is polarized along a plane perpendicular to the first polarization plane by the light detecting member 23d is emitted from an illumination window 18A to an object.

As such, the light detecting member 23d that polarizes illumination light to be emitted to the object and transmits the component which is polarized along the plane perpendicular to the polarization plane of the illumination light is provided in the first optical system 23 for acquiring a polarized image. Therefore, it is possible to prevent the reflection of light from the surface of tissues and acquire a polarized image with high contrast.

Second Modification of First Embodiment

Figure 10:
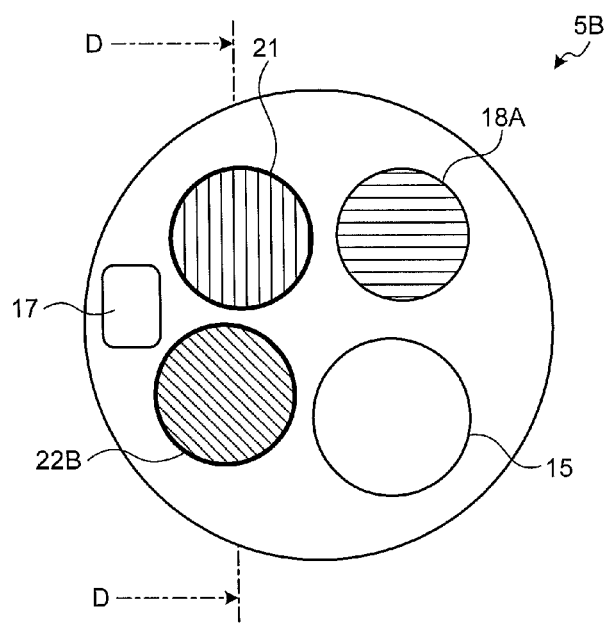
FIG. 10 is a diagram illustrating an example of a distal end surface of a tip portion of an endoscope according to a second modification of the first embodiment.
Figure 11:
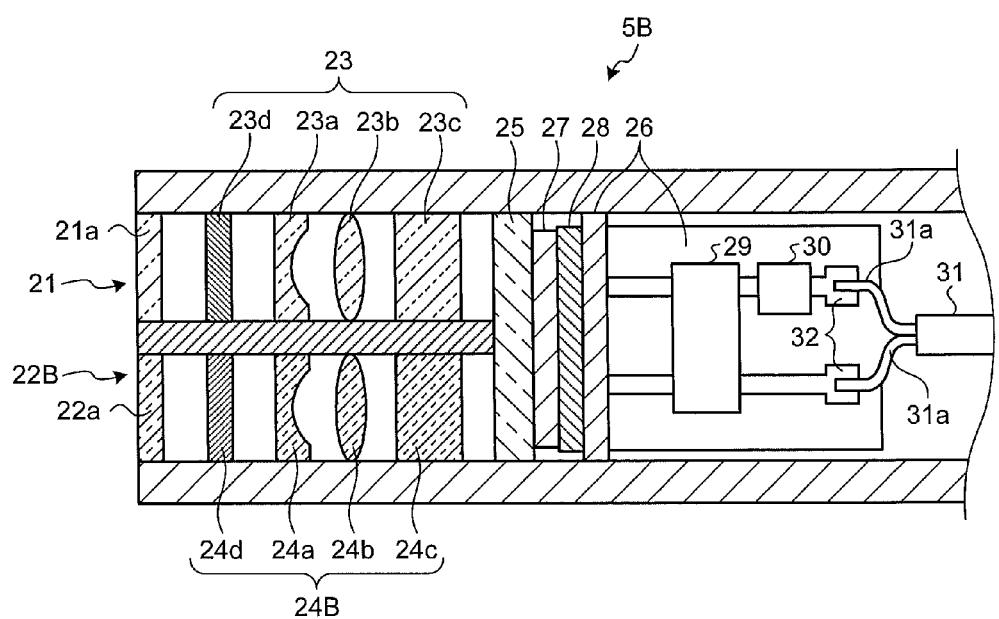
FIG. 11 is a diagram illustrating a portion of a cross-section of the tip portion taken along the line D-D of FIG. 10.

Next, a second modification of the first embodiment will be described. FIG. 10 is a diagram illustrating an example of the distal end surface of a tip portion of an endoscope according to the second modification of the first embodiment. FIG. 11 is a diagram illustrating a portion of the cross-section of a tip portion 5B taken along the line D-D of FIG. 10.

As illustrated in FIGS. 10 and 11, the tip portion 5B of the endoscope according to the second modification of the first embodiment includes a second optical system 24B, instead of the second optical system 24. The second optical system 24B further includes a light detecting member 24d that transmits only the component which is polarized along a third polarization plane different from the first polarization plane by the light detecting member 23d of the first optical system 23 and the second polarization plane by the light detecting member 18b provided between the illumination window 18A and the light guide 19, among incident light components. The light detecting member 24d transmits only the component polarized along a plane which is rotated 45° with respect to the polarization plane by the light detecting member 23d of the first optical system 23, among incident light components. In other words, the second optical system 24B emits only the component polarized along the plane which is rotated 45° with respect to the polarization plane by the light detecting member 23d of the first optical system 23 among the light components incident from an observation window 22B to the region S2 of the light receiving unit 28.

As a result, it is possible to acquire polarized images for different polarization planes and observe tissue characterization while changing the depth direction. In addition, it is possible to perform image processing using the polarized images for different polarization planes to acquire the image of the distribution of tissue characterization.

Second Embodiment

Next, a second embodiment will be described. In the second embodiment, a normal image formed by normal white light and a fluorescence observation image which is used to observe a fluorescent material which emits fluorescence by irradiation of excitation light serving as special light are acquired as acquisition target images.

Figure 12A:
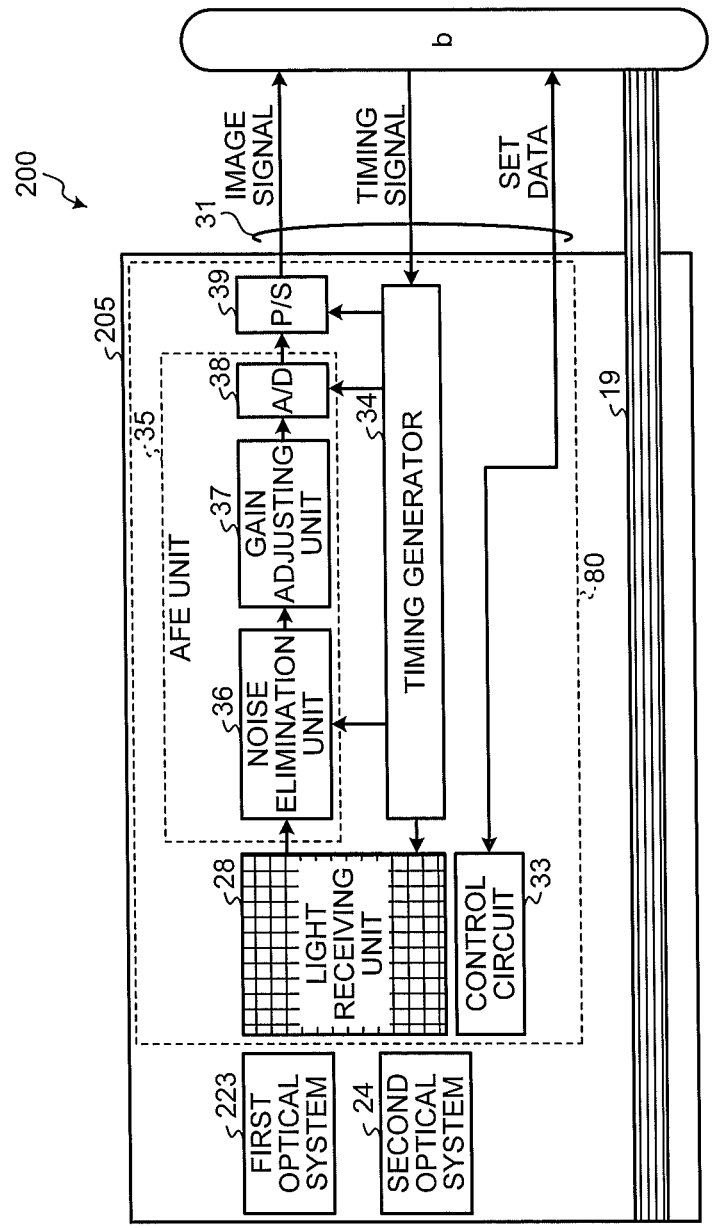
FIGS. 12A and 12B are block diagrams illustrating a structure of an endoscope system according to a second embodiment.
Figure 12B:
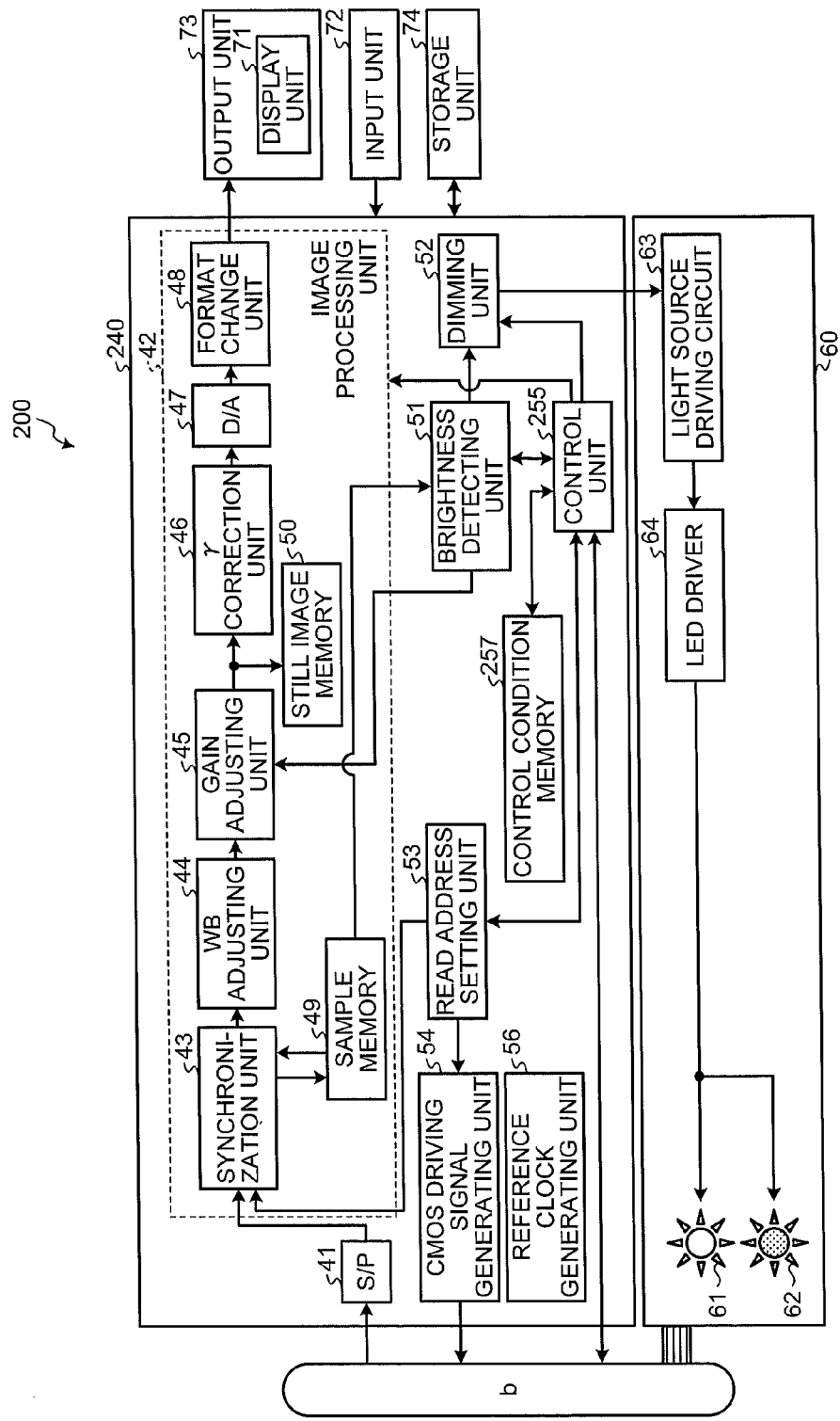

FIGS. 12A and 12B are block diagrams illustrating the structure of an endoscope system according to the second embodiment. As illustrated in FIGS. 12A and 12B, in an endoscope system 200 according to the second embodiment, a tip portion 205 includes a first optical system 223, instead of the first optical system 23 illustrated in FIGS. 6A and 6B. A control device 240 of the endoscope system 200 includes a control unit 255 having the same function as the control unit 55, instead of the control unit 55 illustrated in FIGS. 6A and 6B and also includes a control condition memory 257 that stores control conditions corresponding to the normal image and the fluorescence observation image which are acquisition targets.

In the second embodiment, when the fluorescence observation image is acquired, a special light source 62 emits blue excitation light or purple excitation light with a shorter wavelength than the blue excitation light, in order to detect a fluorescent material having a spectrum in the range of green or red which is originally present in the body tissues or a marker substance which is inserted into a subject and emits red fluorescence or green fluorescence. When the normal image is acquired, a white light source 61 emits white light.

Figure 13:
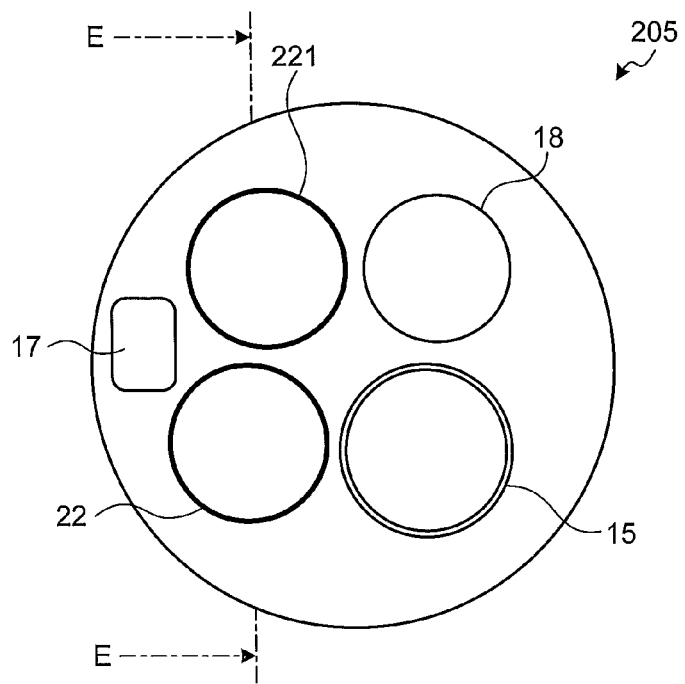
FIG. 13 is a diagram illustrating a distal end surface of a tip portion of an endoscope according to the second embodiment.

FIG. 13 is a diagram illustrating the distal end surface of a tip portion of an endoscope according to the second embodiment. As illustrated in FIG. 13, similarly to the first embodiment, the opening portion 15 for presenting the treatment tool, the cleaning nozzle 17, the illumination window 18 from which illumination light is emitted, an observation window 221, and the observation window 22 are provided in the distal end surface of the tip portion 205 of the endoscope. Light which is incident from the outside through the observation window 221 is incident on the first optical system 223 and is focused. Light which is incident from the outside through the observation window 22 is incident on the first optical system 223 and is focused. Similarly to FIG. 4, the observation window 221 is blocked by a cover glass 21a.

Figure 14:
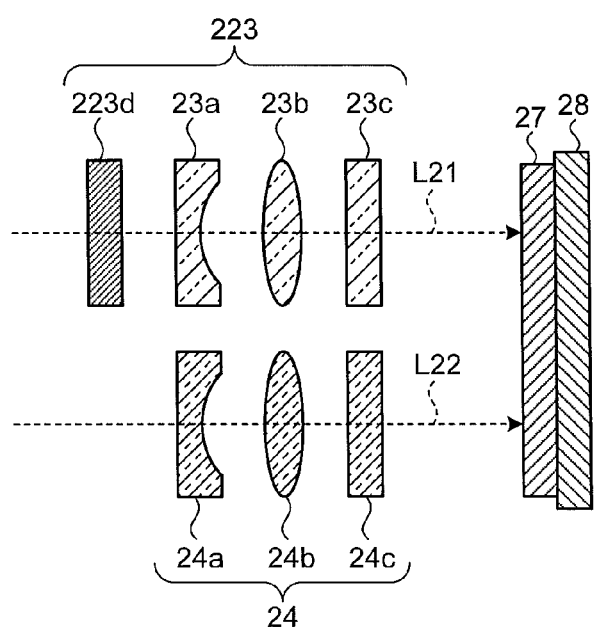
FIG. 14 is a diagram illustrating a first optical system and a second optical system illustrated in FIGS. 12A and 12B.

FIG. 14 is a diagram illustrating the first optical system 223 and a second optical system 24 illustrated in FIGS. 12A and 12B. FIG. 14 is a cross-sectional view illustrating the first optical system 223, the second optical system 24, the on-chip filter 27, and the light receiving unit 28 of the tip portion 205 taken along the line E-E of FIG. 13. In FIG. 14, the cover glasses 21a, 22a, and 25, the circuit board 26, the driver 29, the conversion circuit 30, the assembled cable 31, and the electrodes 32 illustrated in FIG. 4 are not illustrated.

Figures 15, 16:
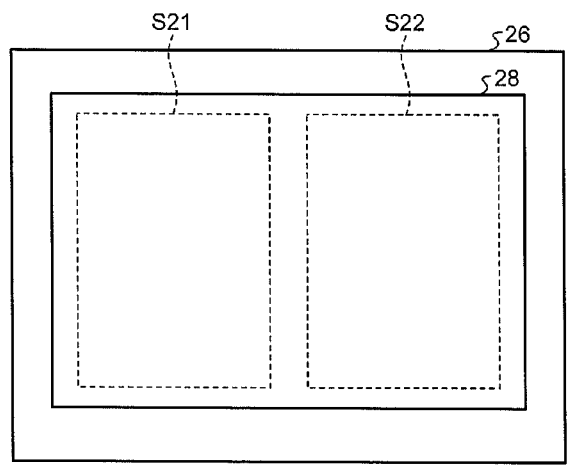
FIG. 15 is a diagram illustrating an example of a light receiving region provided in a light receiving unit illustrated in FIG. 14.
FIG. 16 is a diagram illustrating an example of a control condition list table stored in a control condition memory illustrated in FIGS. 12A and 12B.

The first optical system 223 includes a spectrum filter 223d, instead of the light detecting member 23d of the first optical system 23, disperses light which is incident through the observation window 221, focuses the light, and emits the focused light to a region S21 (see FIG. 15) of the light receiving unit 28. The second optical system 24 includes lenses 24a to 24c, focuses light which is incident through the observation window 22, and emits the focused light to a region S22 (see FIG. 15) of the light receiving unit 28 different from the region S21.

The control unit 255 directs the white light source 61 and the special light source 62 to alternately emit white light and special light and changes a read target pixel for each frame, depending on the type of light emitted, thereby acquiring the normal image and the fluorescence observation image substantially at the same time. The control unit 255 controls the illumination process of each light source and the reading process of a timing generator 34 and an AFE unit 35 in correspondence with the acquisition target image, under the control conditions indicated in a table T2 illustrated in FIG. 16, for example. The table T2 is stored in the control condition memory 257.

First, a frame for acquiring the fluorescence observation image will be described. In this case, as illustrated in table T2, the control unit 255 directs the special light source 62 to emit, as special light, blue excitation light or purple excitation light with a shorter wavelength than the blue excitation light. Then, in order to acquire the brightness of fluorescence emitted from a fluorescence material excited by the excitation light, the control unit 255 changes the pixels in the region S21 of the light receiving unit 28 on which light L21 (see FIG. 14) which has been dispersed and focused by the first optical system 223 is incident to read target pixels set by the read address setting unit 53.

Then, the read address setting unit 53 sets the pixels in the region S21 corresponding to the first optical system 223 among the pixels of the light receiving unit 28 as the read target pixels under the control of the control unit 255, and the timing generator 34 and the AFE unit 35 read pixel information from the pixels in the region S21 which are set as the read target pixels by the read address setting unit 53 among a plurality of pixels for imaging in the light receiving unit 28. In this frame, the timing generator 34 and the AFE unit 35 do not read pixel information from the pixels other than the pixels in the region S21 of the light receiving unit 28. Then, the image processing unit 42 generates the fluorescence observation image in accordance with the pixel information which is read from the pixels in the region S21 of the light receiving unit 28 by the timing generator 34 and the AFE unit 35.

In the frame for acquiring the normal image, as illustrated in the table T2 (see FIG. 16), the control unit 255 directs the white light source 61 to emit white light. Then, when the normal image is generated, the control unit 255 changes the pixels in the region S22 of the light receiving unit 28 on which light L22 (see FIG. 14) focused by the second optical system 24 is incident to the read target pixels set by the read address setting unit 53.

Then, the read address setting unit 53 sets the pixels in the region S22 corresponding to the second optical system 24 among the pixels of the light receiving unit 28 as the read target pixels under the control of the control unit 255, and the timing generator 34 and the AFE unit 35 read pixel information from the pixels in the region S22 which are set as the read target pixels by the read address setting unit 53 among the plurality of pixels for imaging in the light receiving unit 28. In this frame, the timing generator 34 and the AFE unit 35 do not read pixel information from the pixels other than the pixels in the region S22 of the light receiving unit 28. Then, the image processing unit 42 generates the normal image in accordance with the pixel information which is read from the pixels in the region S22 of the light receiving unit 28 by the timing generator 34 and the AFE unit 35.

In the second embodiment, fluorescence with low brightness is received and the fluorescence observation image is generated. Therefore, in the second embodiment, in order to generate a bright fluorescence observation image suitable for observation, the control unit 255 changes the control conditions when the fluorescence observation image is acquired and when the normal observation image is acquired and controls each component.

Specifically, as illustrated in table T2, the control unit 255 controls the light emitting process of the white light source 61 and the special light source 62 and the reading process of the timing generator 34 and the AFE unit 35 such that exposure time in the frame in which the image of the object illuminated with special light emitted from the special light source 62 is captured and pixel information is output is longer than that in the frame in which the image of the object illuminated with white light emitted from the white light source 61 is captured and pixel information is output, thereby increasing the actual light reception sensitivity of fluorescence.

Then, the control unit 255 directs the gain adjusting unit 37 to amplify the brightness value of the pixel in the region S21 in the frame in which the image of the object illuminated with special light emitted from the special light source 62 is captured and the pixel information is output at a gain more than a standard gain for the brightness value of the pixel in the region S21 in the frame in which the image of the object illuminated with white light emitted from the white light source 61 is captured and the pixel information is output and output the amplified value. In addition, the control unit 255 directs the AFE unit 35 to add the brightness values of a plurality of pixels in a block including a plurality of adjacent pixels as the brightness values of the pixels in the region S21 and perform binning output in a block unit. In this way, the control unit 255 increases the brightness value of the pixel in the region S21 which receives fluorescence.

Under the control of the control unit 255, the image processing unit 42 can use the pixel information of the pixel in the region S21 with an enhanced brightness value when image processing is performed for the fluorescence observation image. Therefore, it is possible to generate a bright fluorescence observation image.

As such, in the second embodiment, it is possible to obtain the same effect as that in the first embodiment and control the exposure time, the amplification process, and the binning output process in correspondence with the acquisition target images. Therefore, it is possible to acquire a bright fluorescence observation image suitable for observation.

Furthermore, in the second embodiment, it is possible to uniquely set the optical system so as to correspond to each observation target image. Therefore, it is possible to optimize lenses or spectrum filters forming the first optical system 223 and the second optical system 24 according to the corresponding image. For example, the spectrum filter 223d of the first optical system 223 may be a filter with transmittance having a narrow half width. In this case, it is possible to acquire an image with higher specificity of fluorescence.

Figure 17:
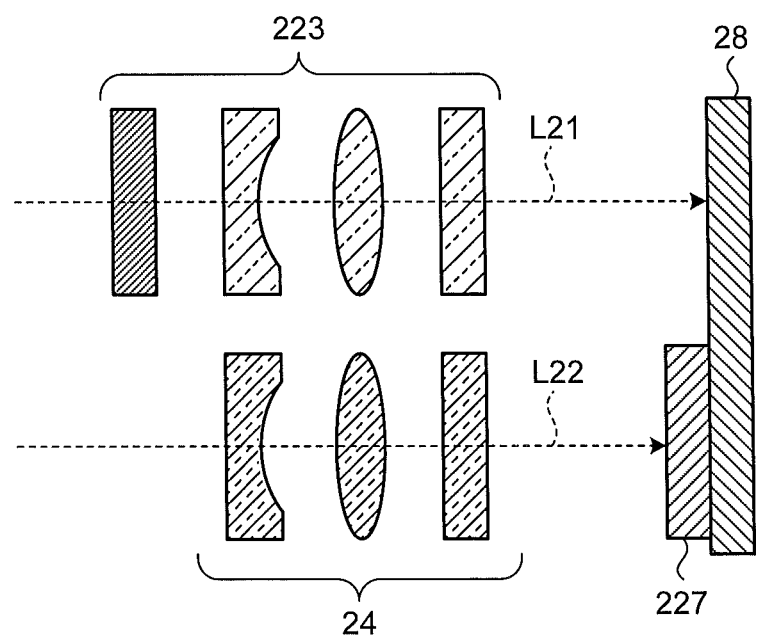
FIG. 17 is a diagram illustrating an example of the first optical system and the second optical system illustrated in FIGS. 12A and 12B.

As illustrated in FIG. 17, a filter may be removed from the region on which light L21 is incident during fluorescent observation and an on-chip filter 227 may be provided only in the region S22 of the light receiving unit 28 on which the light L22 focused by the second optical system 24 is incident. In this case, it is possible to further improve the light reception sensitivity of the pixel in the region S21 which is a read target when the fluorescence observation image is acquired. When the fluorescent image and the normal image with the same resolution are acquired, the regions S21 and S22 of the light receiving unit 28 may have the same area and shape in order to equalize the number of pixels.

Third Embodiment

Next, a third embodiment will be described. In the third embodiment, light components in two bands, that is, blue light and green light in a narrow band which are likely to be absorbed by hemoglobin in the blood are emitted to acquire an NBI observation image in which a capillary vessel in a superficial portion of the mucous membrane and the fine pattern of the mucous membrane are emphasized as an acquisition target image, in addition to the normal image formed by normal white light and the fluorescence observation image.

Figure 18A:
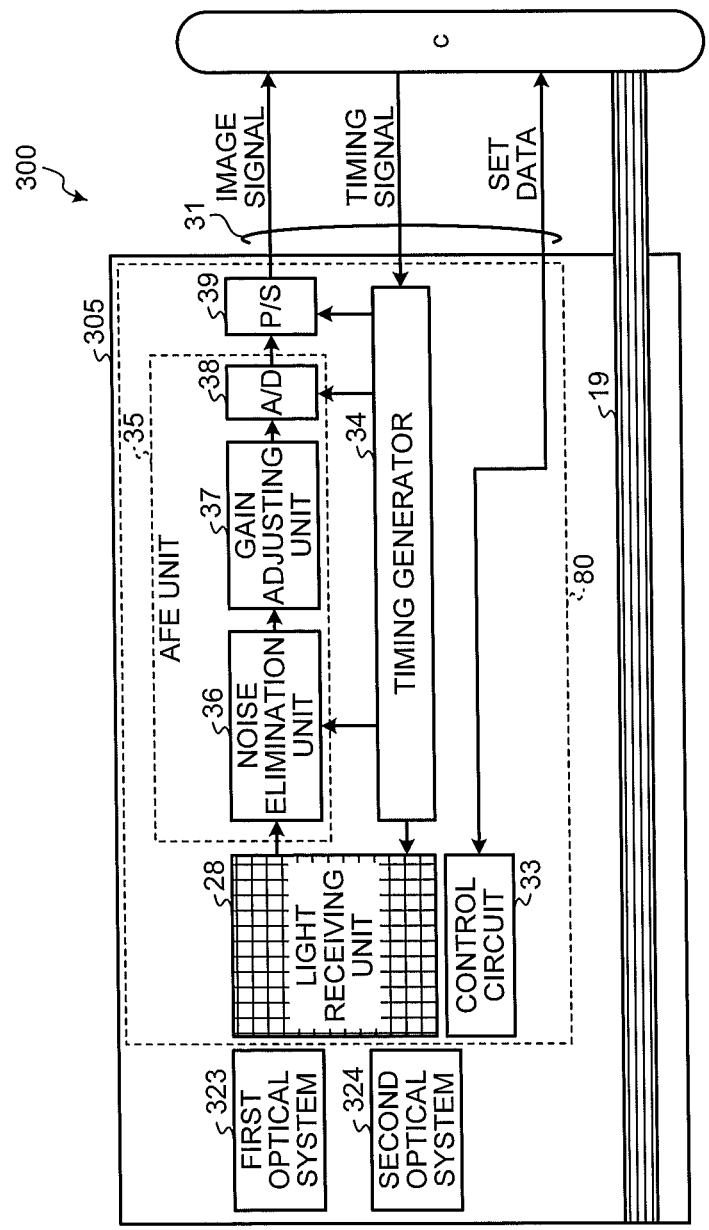
FIGS. 18A and 18B are block diagrams illustrating a structure of an endoscope system according to a third embodiment.
Figure 18B:
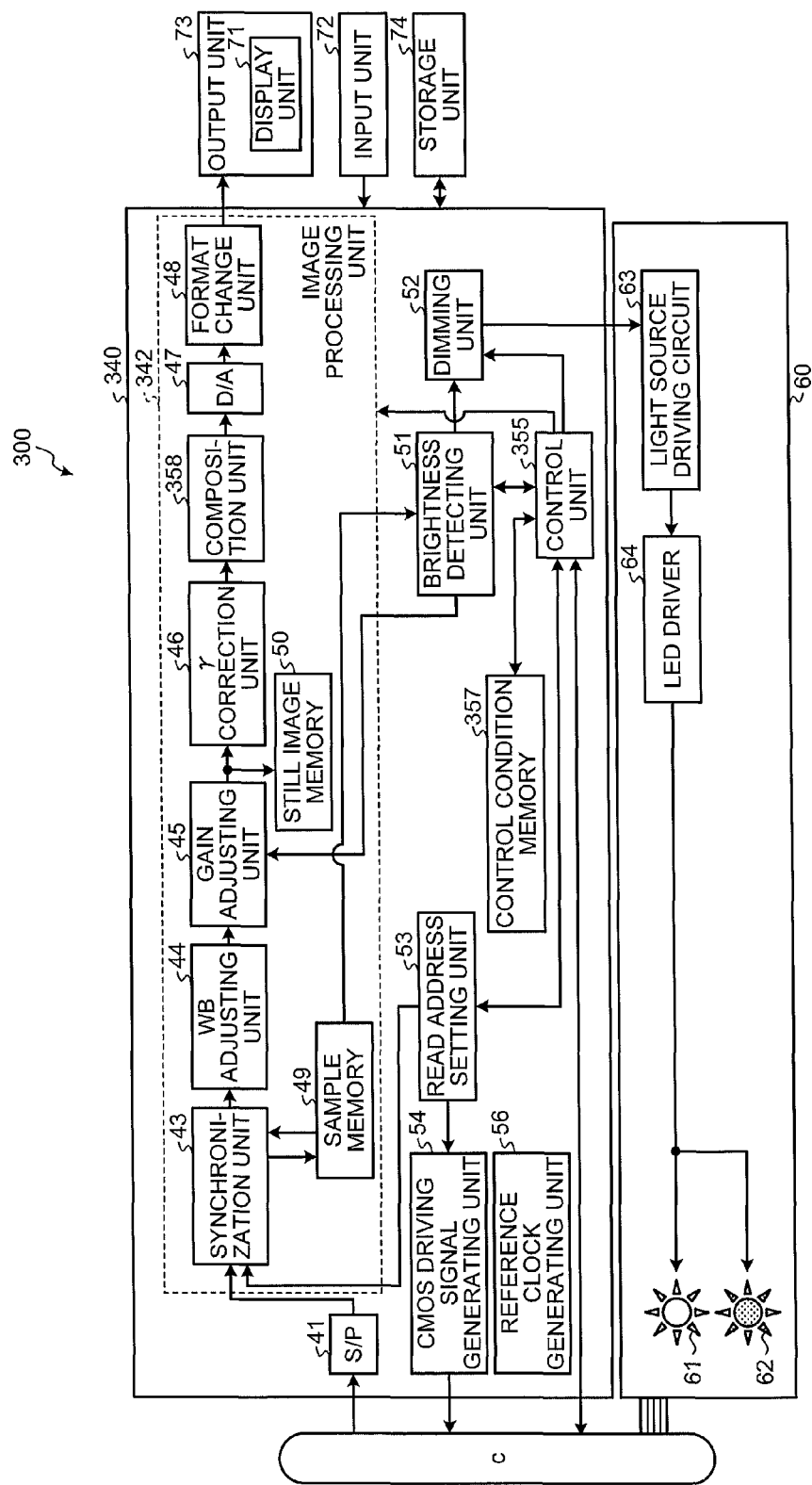

FIGS. 18A and 18B are block diagrams illustrating the structure of an endoscope system according to the third embodiment. As illustrated in FIGS. 18A and 18B, in an endoscope system 300 according to the third embodiment, a tip portion 305 includes a first optical system 323 instead of the first optical system 23 illustrated in FIGS. 6A and 6B and also includes a second optical system 324 instead of the second optical system 24. A control device 340 of the endoscope system 300 includes a control unit 355 having the same function as the control unit 55, instead of the control unit 55 illustrated in FIGS. 6A and 6B, and also includes a control condition memory 357 that stores control conditions corresponding to the normal image, the fluorescence observation image, and the NBI observation image, which are acquisition target images, and an image processing unit 342 further including a composition unit 358 that combines two images and generates one image.

In the third embodiment, similarly to the second embodiment, when the normal image is acquired, the white light source 61 emits white light. When the fluorescence observation image is acquired, the special light source 62 emits blue excitation light which is in a wavelength band narrower than that of white light, or purple excitation light with a shorter wavelength than the blue excitation light. In addition, in the third embodiment, when the NBI observation image is acquired, the special light source 62 emits NBI illumination light components in two bands, that is, blue light and green light which are made to be in a narrow band and are likely to be absorbed by hemoglobin in the blood.

Figure 19:
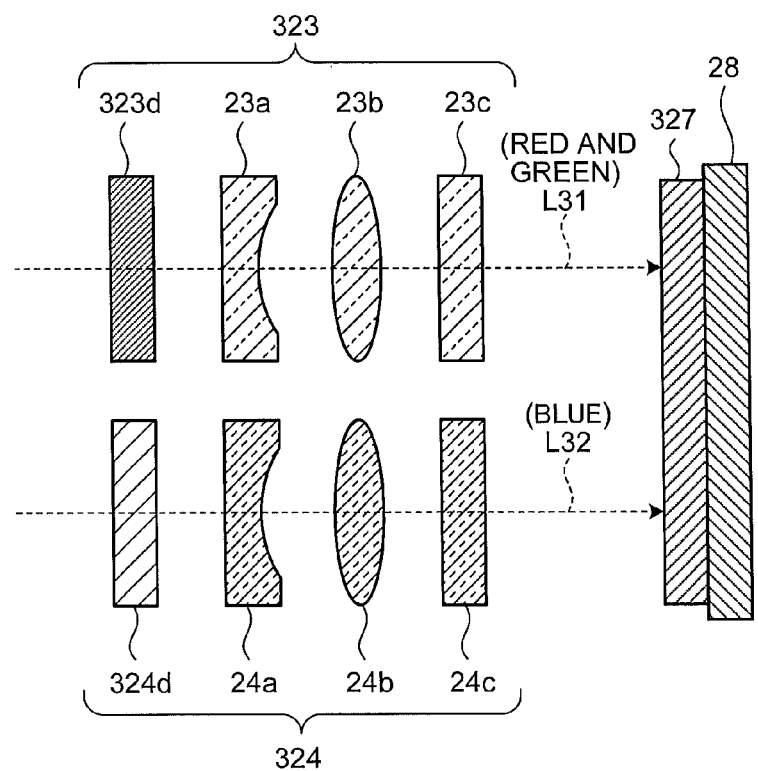
FIG. 19 is a diagram illustrating a first optical system and a second optical system illustrated in FIGS. 18A and 18B.

Next, the first optical system 323 and the second optical system 324 illustrated in FIGS. 18A and 18B will be described. FIG. 19 is a cross-sectional view illustrating the first optical system 323, the second optical system 324, an on-chip filter 327, and the light receiving unit 28 in the tip portion 305. In FIG. 19, cover glasses 21a, 22a, and 25, a circuit board 26, a driver 29, a conversion circuit 30, an assembled cable 31, and electrodes 32 in the tip portion 305 are not illustrated.

Figure 20:
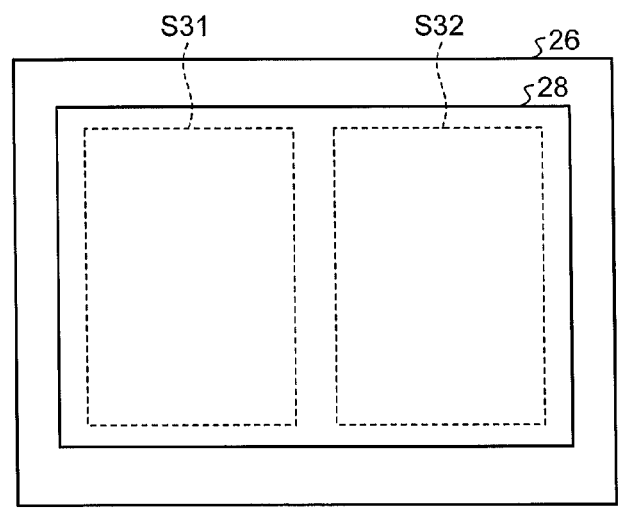
FIG. 20 is a diagram illustrating an example of a light receiving region provided in a light receiving unit illustrated in FIG. 19.

As illustrated in FIG. 19, the first optical system 323 includes lenses 23a to 23c and a filter 323d that transmits red light and green light among incident light components, focuses only the red light and the green light among light components incident through an observation window, and emits the red light and the green light to a region S31 (see FIG. 20) of the light receiving unit 28.

The second optical system 324 includes lenses 24a to 24c and a filter 324d that transmits blue light among incident light components, focuses only the blue light among light components incident through an observation window, and emits the blue light to a region S32 (see FIG. 20) different from the region S31 in the light receiving unit 28. When the acquisition target images with the same resolution are acquired, the regions S31 and S32 of the light receiving unit 28 may have the same area and shape in order to equalize the number of pixels.

Figure 21:
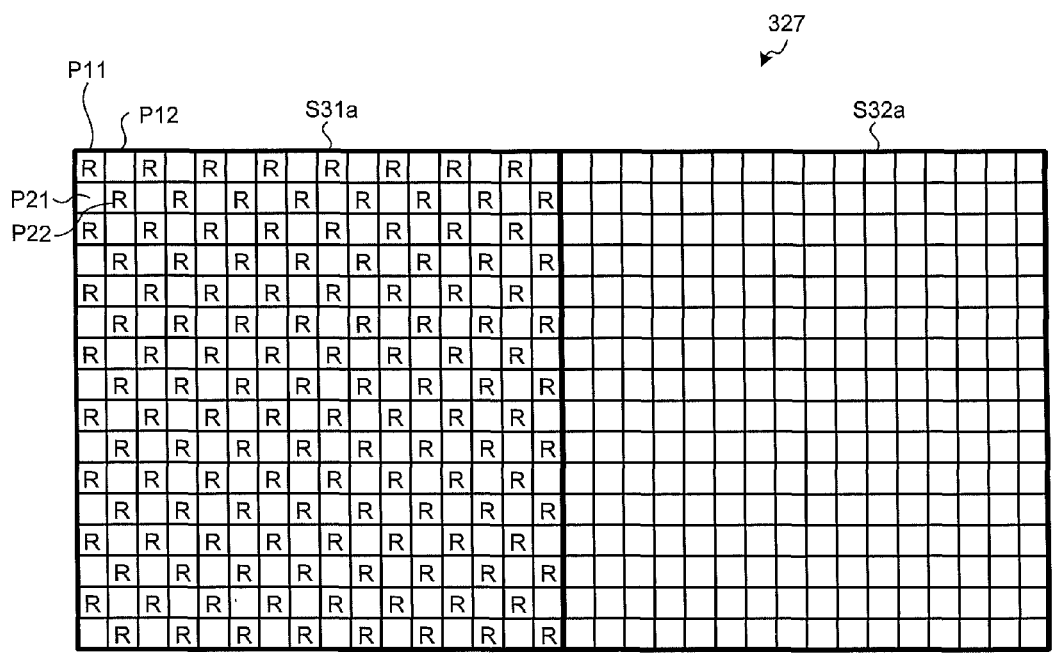
FIG. 21 is a plan view illustrating a filter array of an on-chip filter illustrated in FIG. 19.

Next, the on-chip filter 327 illustrated in FIG. 19 will be described. FIG. 21 is a plan view illustrating the filter array of the on-chip filter 327 illustrated in FIG. 19. As illustrated in FIG. 21, in the on-chip filter 327, an R filter is provided on a pixel P11 in a region S31a which is disposed above the region S31 of the light receiving unit 28 and no filter is provided on a pixel P12 which is adjacent to the right side of the pixel P11 in FIG. 21. In addition, no filter is provided on a pixel P21 which is adjacent to the lower side of the pixel P11 in FIG. 21 and an R filter is provided on a pixel P22 which is adjacent to the right side of the pixel P21 in FIG. 21. As such, in the region S31a, the R filters are provided on every other pixel in the vertical and horizontal directions. Therefore, of red light and green light emitted from the second optical system 324, red light is incident on the pixels (for example, the pixels P11 and P22 in FIG. 21) on which the R filters are provided and both red light and green light are incident on the pixels (for example, the pixels P12 and P21 in FIG. 21) on which no filter is provided.

In the on-chip filter 327, no filter is provided in a region S32a which is disposed above the region S32 of the light receiving unit 28. Therefore, blue light emitted from the second optical system 324 is incident on all pixels without being filtered.

In the third embodiment, the control unit 355 controls an illumination process of the white light source 61 and the special light source 62, a read target pixel setting process of the read address setting unit 53, a reading process of the timing generator 34 and the AFE unit 35, and an image generating process of the image processing unit 342 so as to correspond to the acquisition target images. The control unit 355 controls each light source, the read address setting unit 53, the timing generator 34, the AFE unit 35, and the image processing unit 342 so as to correspond to the acquisition target images under, for example, the control conditions in a table T3 illustrated in FIG. 22. The table T3 is stored in the control condition memory 357.

First, a case in which a normal observation image is acquired will be described. In this case, as illustrated in the table T3, the control unit 355 directs the white light source 61 to emit white light. Then, when a normal image is generated, the control unit 355 changes all pixels in the region S31 of the light receiving unit 28 on which light L31 (see FIG. 19) focused by the first optical system 323 is incident and all pixels in the region S32 of the light receiving unit 28 on which light L32 focused by the second optical system 324 is incident to the read target pixels set by the read address setting unit 53.

Then, the read address setting unit 53 sets all pixels in the region S31 and all pixels in the region S32 among the pixels of the light receiving unit 28 as the read target pixels under the control of the control unit 355, and the timing generator 34 and the AFE unit 35 read pixel information from all pixels in the region S31 and all pixels in the region S32 which are set as the read target pixels by the read address setting unit 53 among a plurality of pixels for imaging in the light receiving unit 28.

In this case, among white light components incident from the outside, only red light and green light which are focused by the first optical system 323 are incident on the region S31 of the light receiving unit 28. In this case, only the red light is incident on R pixels in the region S31 on which the R filters are provided and both the red light and the green light are incident on the pixels in the region S31 on which no filter is provided, according to the filter array in the region S31a of the on-chip filter 327. Therefore, in the image processing unit 342, a synchronization unit 43 generates an R image and a G image in accordance with the pixel information read from all pixels in the region S31.

Among the white light components incident from the outside, only the blue light focused by the second optical system 324 is incident on the region S32 of the light receiving unit 28. In this case, since no filter is provided in the region S32a of the on-chip filter 327, the blue light is incident on all pixels in the region S32. Therefore, in the image processing unit 342, the synchronization unit 43 generates a B image in accordance with the pixel information read from all pixels in the region S32.

Then, in the image processing unit 342, the composition unit 358 combines the R and G images corresponding to the pixel information from all pixels in the region S31 and the B image corresponding to the pixel information from all pixels in the region S32 and generates the normal observation image. The display unit 71 displays the generated normal observation image during white light observation.

Next, a case in which the NBI observation image is acquired will be described. In this case, as illustrated in table T3, the control unit 355 directs the special light source 62 to emit NBI illumination light components in two bands, that is, blue light and green light in a narrow band. Then, when an NBI image is generated, the control unit 355 changes pixels other than the R pixels in the region S31 of the light receiving unit 28 on which the light L31 (see FIG. 19) focused by the first optical system 323 is incident and all pixels in the region S32 of the light receiving unit 28 on which the light L32 focused by the second optical system 324 is incident to the read target pixels set by the read address setting unit 53.

Then, the read address setting unit 53 sets pixels other than the R pixels in the region S31 and all pixels in the region S32 among the pixels of the light receiving unit 28 as the read target pixels under the control of the control unit 355, and the timing generator 34 and the AFE unit 35 read pixel information from the pixels other than the R pixels in the region S31 and all pixels in the region S32 which are set as the read target pixels by the read address setting unit 53 among a plurality of pixels for imaging in the light receiving unit 28.

In this case, of green light and blue light incident from the outside, only the green light focused by the first optical system 323 is incident on the region S31 of the light receiving unit 28. In this case, according to the filter array of the region S31a of the on-chip filter 327, no light is incident on the R pixels in the region S31 on which the R filters are provided and the green light is incident on the pixels on which no filter is provided in the region S31. Therefore, in this case, the timing generator 34 and the AFE unit 35 read the pixel information from the pixels other than the R pixels in the region S31 and acquire pixel information which is a source of the G image. Then, in the image processing unit 342, the synchronization unit 43 generates the G image in accordance with the read pixel information.

Of green light and blue light incident from the outside, only the blue light focused by the second optical system 324 is incident on the region S32 of the light receiving unit 28. In this case, since no filter is provided in the region S32a of the on-chip filter 327, the blue light is incident on all pixels in the region S32. Therefore, in the image processing unit 342, the synchronization unit 43 generates the B image in accordance with the pixel information read from all pixels in the region S32.

Then, in the image processing unit 342, the composition unit 358 combines the G image corresponding to the pixel information of the pixels other than the R pixels in the region S31 and the B image corresponding to the pixel information of all pixels in the region S32 and generates the NBI observation image. The display unit 71 displays the generated NBI observation image.

When the NBI observation image is acquired, the control unit 355 controls the reading time of the timing generator 34 such that the exposure time is longer than the standard exposure time when the normal observation image is acquired, thereby increasing the light reception sensitivity of blue light and green light by the light receiving unit 28. In addition, when the NBI observation image is acquired, the control unit 355 directs the gain adjusting unit 37 to amplify the brightness values of the pixels in the regions S31 and S32 at a gain more than the standard gain when the normal observation image is acquired and output the brightness values.

According to this control operation, the control unit 355 increases the brightness values of the pixels receiving blue light and green light and acquires a bright NBI observation image suitable for observation. In addition, the on-chip filter 327 may be removed from the region S32 and the control unit 355 directs the AFE unit 35 to perform binning output for the brightness value of the pixel in the region S32 in a block unit. In this case, it is possible to improve the light reception sensitivity of blue light with low sensitivity and a small amount of illumination light.

Next, a case in which the fluorescence observation image is acquired will be described. In this case, as illustrated in the table T3 of FIG. 22, the control unit 355 directs the special light source 62 to emit blue excitation light or purple excitation light with a shorter wavelength than the blue excitation light. As a result, a fluorescent material, which is an observation target, is excited and emits red fluorescence and green fluorescence. Then, when the fluorescence observation image is generated, the control unit 355 changes all pixels in the region S31 of the light receiving unit 28 on which red light and green light focused by the first optical system 323 are incident to the read target pixels set by the read address setting unit 53.

Then, the read address setting unit 53 sets all pixels in the region S31 among the pixels in the light receiving unit 28 as the read target pixels under the control of the control unit 355, and the timing generator 34 and the AFE unit 35 read the pixel information from all pixels in the region S31 which are set as the read target pixels by the read address setting unit 53 among a plurality of pixels for imaging in the light receiving unit 28. Since blue light is not incident on the tip portion 305, no light is incident on the pixels in the region S32. Therefore, the timing generator 34 and the AFE unit 35 do not read the pixel information from the pixels in the region S32.

Only red light is incident on the R pixels in the region S31 and both red light and green light are incident on the pixels on which no filter is provided in the region S31. Therefore, the image processing unit 342 generates an R image and a G image in accordance with the pixel information read from all pixels in the region S31 and generates a fluorescence observation image for observing red fluorescence and green fluorescence in accordance with the R image and the G image. The display unit 71 displays the generated fluorescence observation image.

When the fluorescence observation image is acquired, the control unit 355 controls the reading time of the timing generator 34 such that the exposure time is more than the standard exposure time when a normal image is acquired, thereby improving the light reception sensitivity of red fluorescence and green fluorescence by the light receiving unit 28. In addition, when the fluorescence observation image is acquired, the control unit 355 directs the gain adjusting unit 37 to amplify the brightness values of all pixels in the region S31 at a gain more than the standard gain when a normal observation image is acquired, and output the brightness values. According to this control operation, the control unit 355 increases the brightness values of the pixels receiving red fluorescence and green fluorescence and acquires a bright fluorescence observation image suitable for observation.

As such, in the third embodiment, it is possible to obtain the same effect as that in the first embodiment. Meanwhile, since the illumination process, the read target pixel setting, and image processing are performed so as to correspond to the acquisition target images, it is possible to acquire three kinds of images, that is, a normal image, a fluorescence observation image, and an NBI observation image. In addition, in the third embodiment, since the exposure time, the amplification process, and the binning output process are controlled so as to correspond to the acquisition target images, it is possible to acquire a bright NBI observation image and a bright fluorescence observation image suitable for observation.

First Modification of Third Embodiment

A case in which both a fluorescence observation image and a shape observation monochrome image are acquired will be described as a first modification of the third embodiment.

Figure 23:
FIG. 23 is a diagram illustrating another example of the control condition list table stored in the control condition memory illustrated in FIGS. 18A and 18B.

As illustrated in a table T31 of FIG. 23, the control unit 355 directs the special light source 62 to emit excitation light. Then, for a monochrome image, the control unit 355 directs the read address setting unit 53 to set all pixels in the region S32 on which only blue light is incident as the read target pixels and directs the timing generator 34 and the AFE unit 35 to read the pixel information from all pixels in the regions S31 and S32. Then, the control unit 355 directs the image processing unit 342 to generate one monochrome image in accordance with the pixel information of all pixels in the region S32. According to this control operation, it is possible to acquire the fluorescence observation image and the shape observation monochrome image at the same time and achieve smooth observation.

Second Modification of Third Embodiment

Next, a case in which the fluorescence observation image is corrected in accordance with the brightness values of the pixels in the region S32 on which no light is incident to acquire a normalized fluorescence observation image will be described as a second modification of the third embodiment.

Figure 24:
FIG. 24 is a diagram illustrating another example of the control condition list table stored in the control condition memory illustrated in FIGS. 18A and 18B.

As illustrated in a table T32 of FIG. 24, the control unit 355 directs the read address setting unit 53 to set all pixels in the region S31 and all pixels in the region S32 on which no light is incident as the read target pixels and directs the timing generator 34 and the AFE unit 35 to read the pixel information from all pixels in the region S31 and all pixels in the region S32. The gain adjusting unit 37 amplifies the brightness values in the pixel information about the region S32 at a high gain which is equal to that for the region S31 and outputs the brightness values.

Then, the control unit 355 directs the image processing unit 342 to correct the brightness values of all pixels in the region S31 for forming an R image and a G image using the brightness values of all pixels in the region S31 on which no light is incident and generate one fluorescence observation image. According to this control operation, it is possible to acquire a normalized fluorescence observation image and achieve appropriate observation.

Fourth Embodiment

Next, a fourth embodiment will be described. In the fourth embodiment, two optical systems are formed so as to have different focal lengths and two images with different focal lengths are acquired at the same time and combined to acquire an image with an extended depth of field focused from a near point to a far point.

Figure 25A:
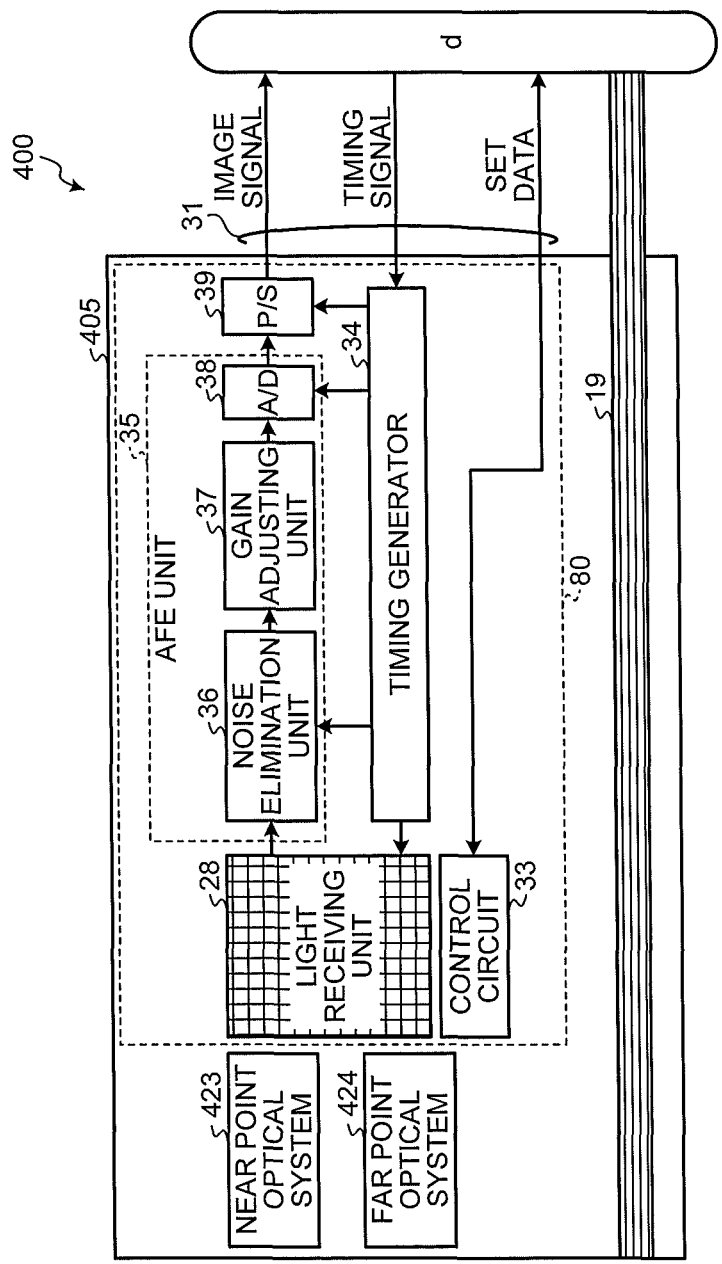
FIGS. 25A and 25B are block diagrams illustrating a structure of an endoscope system according to a fourth embodiment.
Figure 25B:
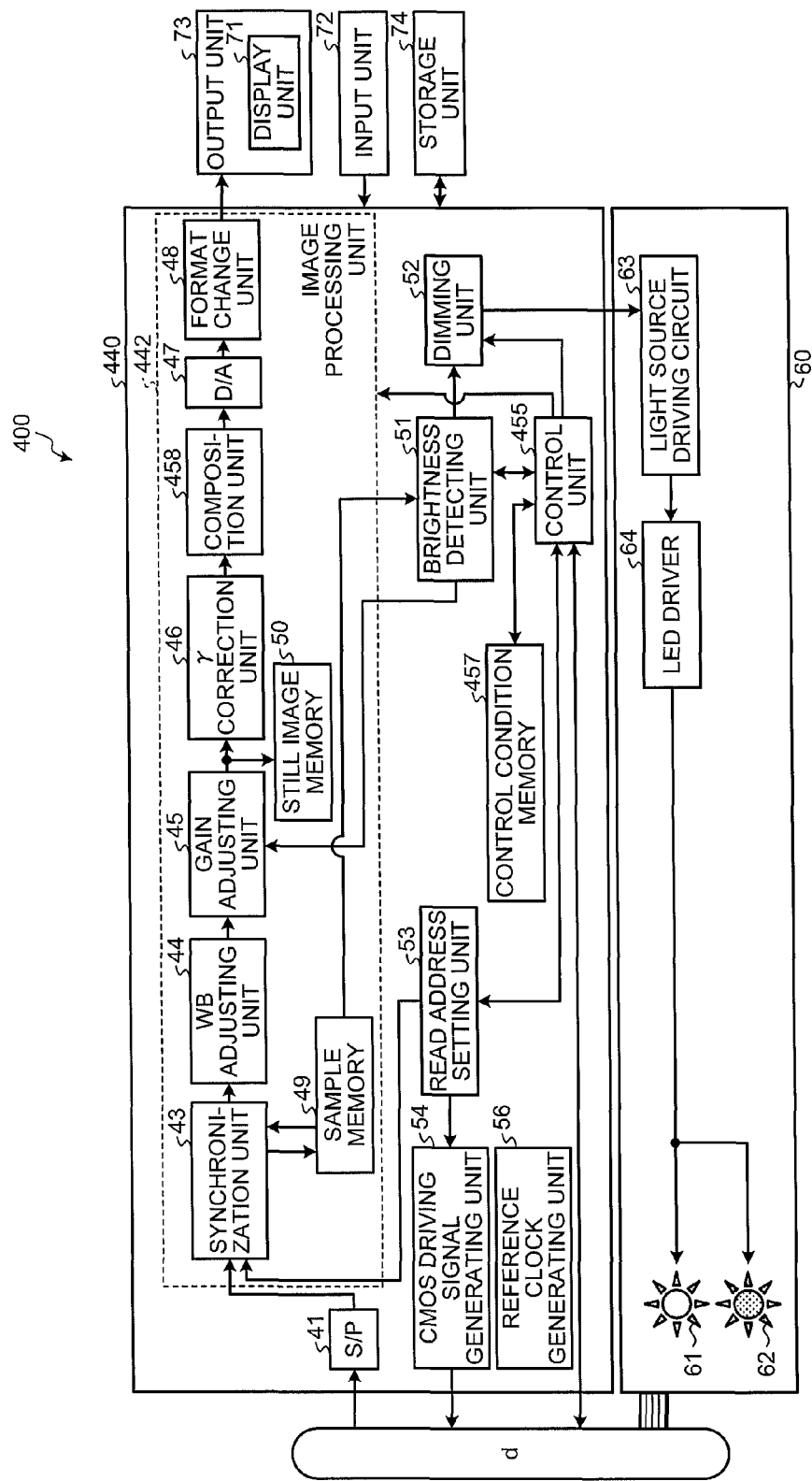

FIGS. 25A and 25B are block diagrams illustrating the structure of an endoscope system according to the fourth embodiment. As illustrated in FIGS. 25A and 25B, in an endoscope system 400 according to the fourth embodiment, a tip portion 405 includes a near point optical system 423 instead of the first optical system 23 illustrated in FIGS. 6A and 6B and also includes a far point optical system 424 instead of the second optical system 24. A control device 440 of the endoscope system 400 includes a control unit 455 having the same function as the control unit 55, instead of the control unit 55 illustrated in FIGS. 6A and 6B, and also includes a control condition memory 457 that stores control conditions for acquiring an image with an extended depth of field and an image processing unit 442 further including a composition unit 458 that combines two images to generate one image.

Figure 26:
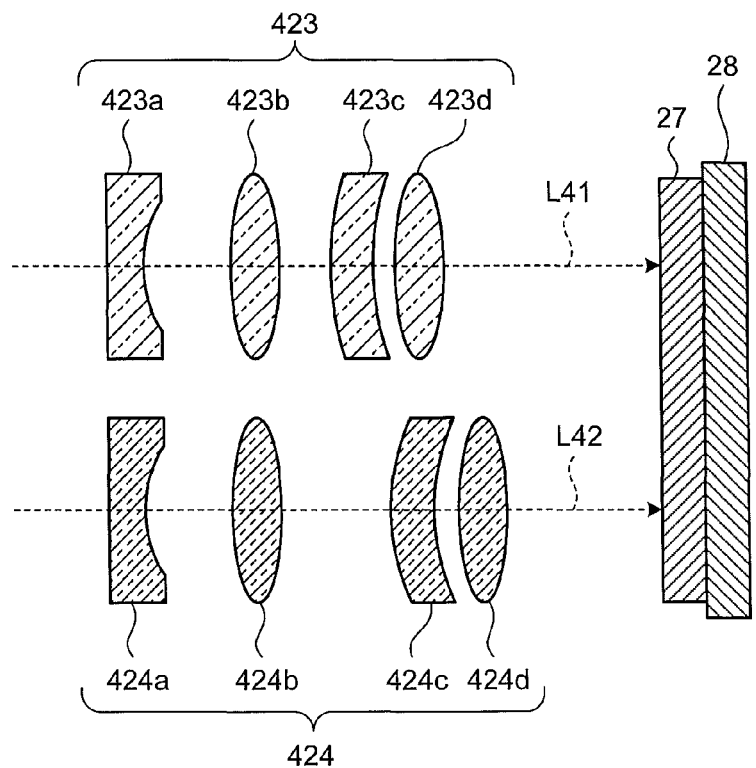
FIG. 26 is a diagram illustrating an example of a near point optical system and a far point optical system illustrated in FIGS. 25A and 25B.

Next, the near point optical system 423 and the far point optical system 424 illustrated in FIGS. 25A and 25B will be described. FIG. 26 is a cross-sectional view illustrating the near point optical system 423, the far point optical system 424, the on-chip filter 27, and the light receiving unit 28 in the tip portion 405. In FIGS. 25A and 15B, the cover glasses 21a, 22a, and 25, the circuit board 26, the driver 29, the conversion circuit 30, the assembled cable 31, and the electrodes 32 in the tip portion 405 are not illustrated.

Figure 27:
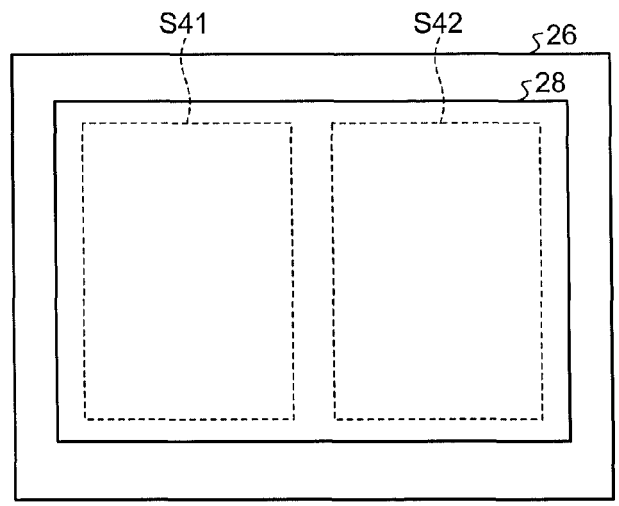
FIG. 27 is a diagram illustrating an example of a light receiving region provided in a light receiving unit illustrated in FIGS. 25A and 25B.

As illustrated in FIG. 26, in the near point optical system 423 and the far point optical system 424, lenses 423a to 423d and lenses 424a to 424d are configured such that the focal lengths are different from each other. The focal position of the near point optical system 423 is set so as to be closer to an observation window than the focal position of the far point optical system 424. The near point optical system 423 emits light L41 for forming a near point image to a region S41 (see FIG. 27) of the light receiving unit 28. The far point optical system 424 emits light L42 for forming a far point image to a region S42 (see FIG. 27) different from the region S41 in the light receiving unit 28. It is preferable that the regions S41 and S42 of the light receiving unit 28 have the same area and shape for a superimposition process of the composition unit 458, which will be described below.

Figure 28:
FIG. 28 is a diagram illustrating an example of a control condition list table stored in a control condition memory illustrated in FIGS. 25A and 25B.

The control unit 455 controls the read address setting unit 53, the timing generator 34, the AFE unit 35, and the image processing unit 442 under, for example, the control conditions in a table T4 illustrated in FIG. 28. The table T4 is stored in the control condition memory 457.

Specifically, as illustrated in the table T4, the control unit 455 changes both pixels in the region S41 corresponding to the near point optical system 423 and pixels in the region S42 corresponding to the far point optical system 424 to the read target pixels set by the read address setting unit 53.

Then, the read address setting unit 53 sets both the pixels in the region S41 and the pixels in the region S42 among the pixels of the light receiving unit 28 as the read target pixels under the control of the control unit 455, and the timing generator 34 and the AFE unit 35 read the pixel information from the pixels in the region S41 and the pixels in the region S42 which are set as the read target pixels by the read address setting unit 53 among a plurality of pixels for imaging in the light receiving unit 28. The timing generator 34 and the AFE unit 35 do not read the pixel information from pixels other than the pixels in the regions S41 and S42 of the light receiving unit 28.

Since the near point optical system 423 is closer to the observation window than the far point optical system 424 and tends to be overexposed, the control unit 455 directs the gain adjusting unit 37 to amplify the brightness values of the pixels in the region S41 at a low gain such that the gain of the pixel in the region S41 corresponding to the near point image decreases. In addition, since the far point optical system 424 is further away from the observation window than the near point optical system 423 and tends to be underexposed, the control unit 455 directs the gain adjusting unit 37 to amplify the brightness values of the pixels in the region S42 at a high gain such that the gain of the pixel in the region S42 corresponding to the far point image increases. As such, the control unit 455 directs the gain adjusting unit 37 to amplify the brightness values of the pixels in the region S41 at a gain different from the gain for the brightness values of the pixels in the region S42 and output the brightness values, thereby adjusting the brightness values. In this way, the dynamic range of the entire image is widened.

In the image processing unit 442, the composition unit 458 superimposes the near point image corresponding to the pixel information which is read from the pixels in the region S41 by the timing generator 34 and the AFE unit 35 and the far point image corresponding to the pixel information read from the pixels of the region S42 to generate one image under the control of the control unit 455.

Figure 29:
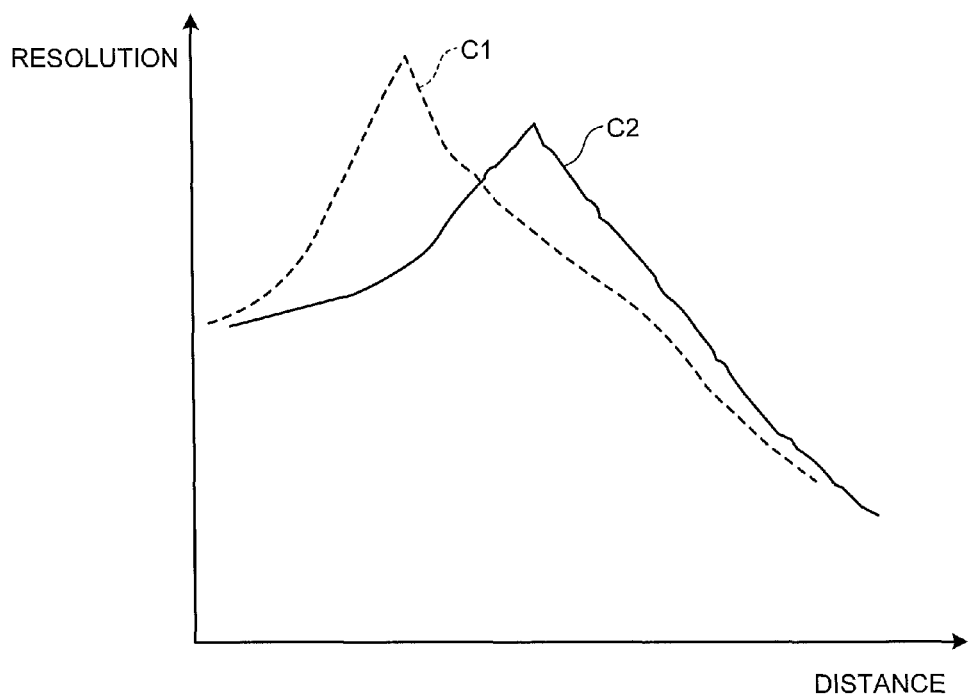
FIG. 29 is a diagram illustrating a relation between resolution and a distance from an illumination light source in a near point image and a far point image.

FIG. 29 is a diagram illustrating the relation between resolution and a distance from an illumination light source in the near point image and the far point image. As represented by a curve C1 in FIG. 29, the resolution of the near point image is high at a distance close to the observation window. On the other hand, as represented by a curve C2 in FIG. 29, the resolution of the far point image is high at a distance away from the observation window. Therefore, the near point image corresponding to the pixel information of the pixels in the region S41 and the far point image corresponding to the pixel information of the pixels in the region S42 are superimposed to acquire an image focused from the far point to the near point.

As such, in the fourth embodiment, it is possible to acquire the near point image and the far point image at the same time with a simple structure including one CMOS imaging element 80 and appropriately acquire an image with an extended depth of field focused from the near point to the far point. In addition, in the fourth embodiment, the pixel information of the pixels in the region S41 corresponding to the near point image and the pixel information of the pixels in the region S42 corresponding to the far point image are amplified at appropriate gains and the images are combined. In this way, it is possible to acquire an image with appropriate brightness and depth.

Fifth Embodiment

Next, a fifth embodiment will be described. In the fifth embodiment, two optical systems are configured so as to have different viewing angles and two images with different viewing angles are acquired at the same time and are displayed. In this way, it is possible to observe a high-resolution main image and a wide-angle image for assisting, for example, the surgical treatment at the same time.

Figure 30A:
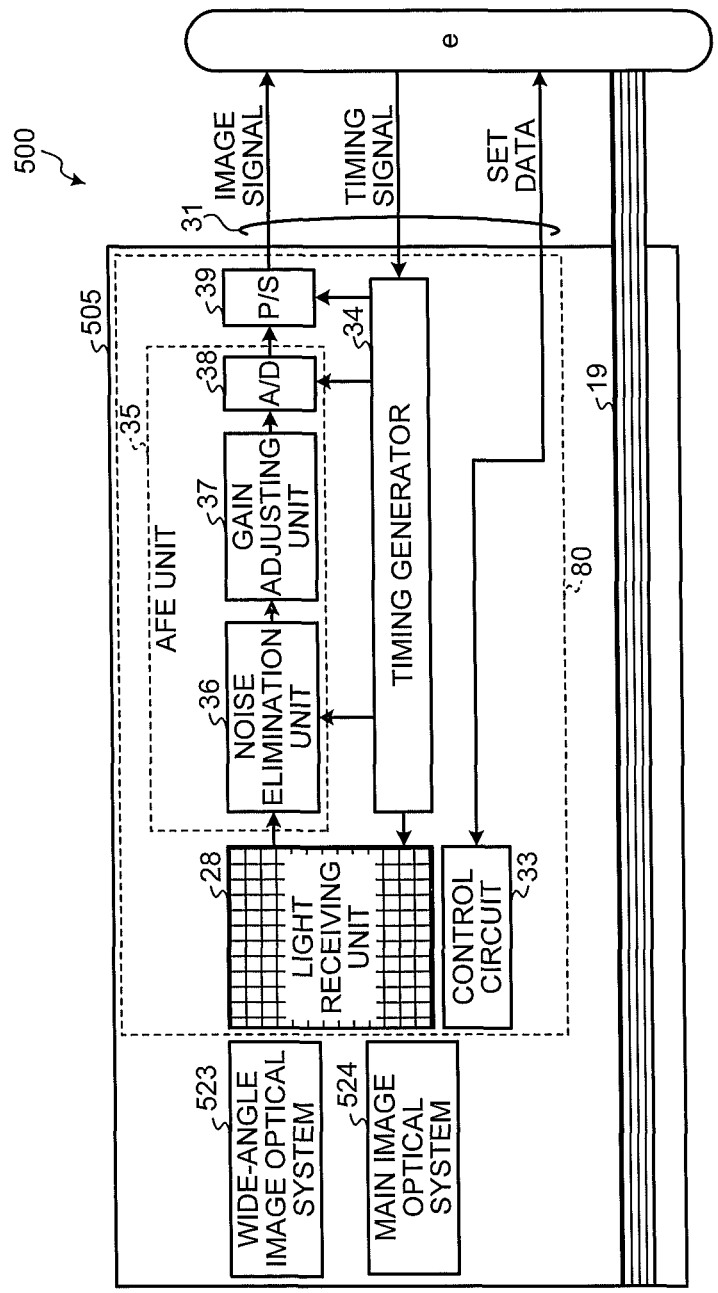
FIGS. 30A and 30B are block diagrams illustrating a structure of an endoscope system according to a fifth embodiment.
Figure 30B:
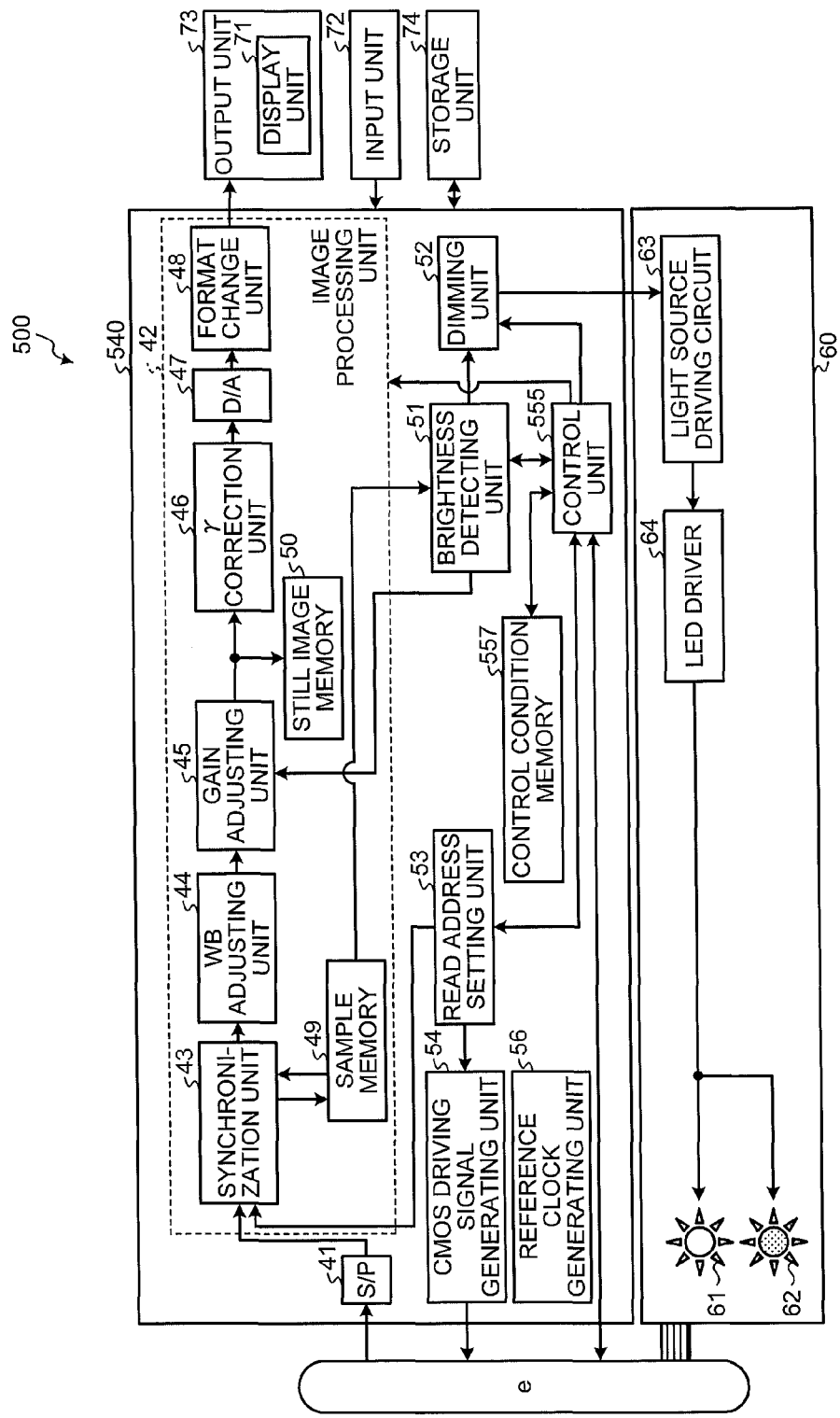

FIGS. 30A and 30B are block diagrams illustrating the structure of an endoscope system according to the fifth embodiment. As illustrated in FIGS. 30 A and 30B, in an endoscope system 500 according to the fifth embodiment, a tip portion 505 includes a wide-angle image optical system 523 instead of the first optical system 23 illustrated in FIGS. 6A and 6B and also includes a main image optical system 524 instead of the second optical system 24. A control device 540 of the endoscope system 500 includes a control unit 555 having the same function as the control unit 55, instead of the control unit 55 illustrated in FIGS. 6A and 6B, and also includes a control condition memory 557 that stores control conditions for acquiring two images, that is, a main image, which is a high-resolution image for detailed observation, and a wide-angle image, which is an auxiliary image.

Figure 31:
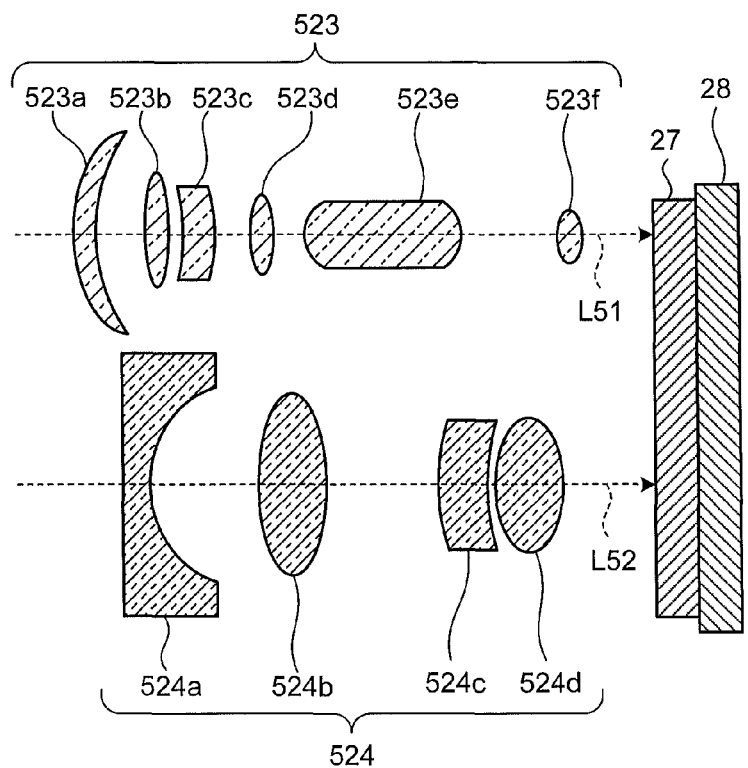
FIG. 31 is a diagram illustrating an example of a wide-angle image optical system and a main image optical system illustrated in FIGS. 30A and 30B.

Next, the wide-angle image optical system 523 and the main image optical system 524 illustrated in FIGS. 30A and 30B will be described. FIG. 31 is a cross-sectional view illustrating the wide-angle image optical system 523, the main image optical system 524, the on-chip filter 27, and the light receiving unit 28 in the tip portion 505. In FIG. 31, the cover glasses 21a, 22a, and 25, the circuit board 26, the driver 29, the conversion circuit 30, the assembled cable 31, and the electrodes 32 in the tip portion 505 are not illustrated.

Figure 32:
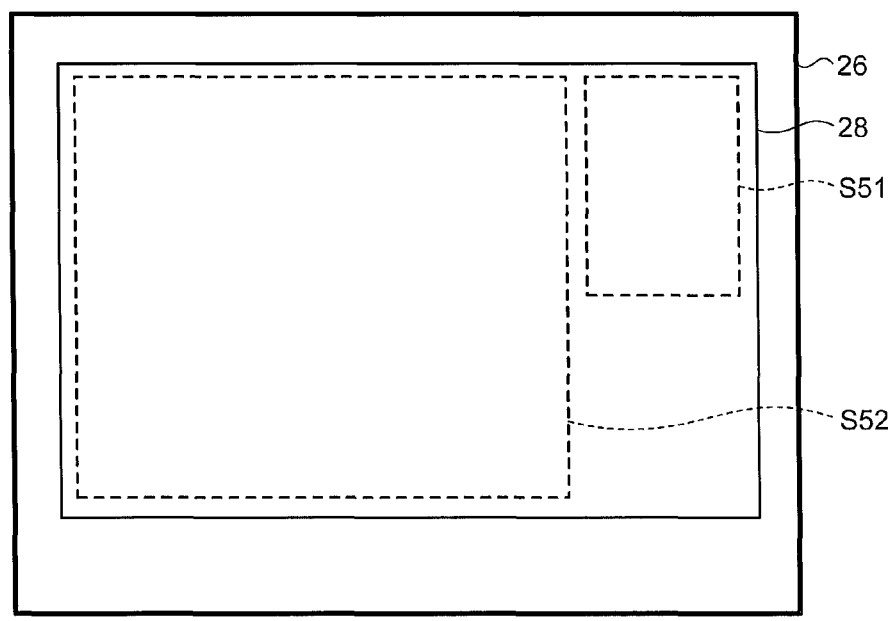
FIG. 32 is a diagram illustrating an example of a light receiving region provided in a light receiving unit illustrated in FIG. 31.

As illustrated in FIG. 31, the wide-angle image optical system 523 includes lenses 523a to 523f including a wide-angle lens and a relay lens in addition to a concave lens and a convex lens and has a wider viewing angle than the main image optical system 524 including lenses 524a to 524d. The wide-angle image optical system 523 emits light L51 for forming the wide-angle image to a region S51 (see FIG. 32) of the light receiving unit 28. The main image optical system 524 emits light L52 for forming the main image to a region S52 (see FIG. 32) different from the region S51 in the light receiving unit.

Since the wide-angle image is an auxiliary image for assisting, for example, the surgical treatment, it is only necessary for the wide-angle image to constantly exhibit a wider range than the treatment range. Since it is only necessary to check a wider range than the treatment range with the wide-angle image, which is an auxiliary image, there is no problem even though the wide-angle image has a lower resolution than the main image requiring high resolution. Therefore, the region S51 on which light emitted from the wide-angle image optical system 523 is incident may be smaller than the region S52 on which light emitted from the main image optical system 524 is incident. When the region S51 and the region S52 are set in this way, it is possible to ensure a large reading region for forming the main image and acquire a high-resolution main image.

The control unit 555 reads both the pixels in the region S51 corresponding to the wide-angle image optical system 523 and the pixels in the region S52 corresponding to the main image optical system 524 and changes the pixels to the read target pixels set by the read address setting unit 53.

Then, the read address setting unit 53 sets both the pixels in the region S51 and the pixels in the region S52 among the pixels of the light receiving unit 28 as the read target pixels under the control of the control unit 555, and the timing generator 34 and the AFE unit 35 read pixel information from the pixels in the region S51 and the pixels in the region S52 which are set as the read target pixels by the read address setting unit 53 among a plurality of pixels for imaging in the light receiving unit 28. The timing generator 34 and the AFE unit 35 do not read pixel information from pixels other than the pixels in the regions S51 and S52 of the light receiving unit 28. The image processing unit 42 generates the wide-angle image, which is an auxiliary image, in accordance with the pixel information which is read from the pixels in the region S51 of the light receiving unit 28 by the timing generator 34 and the AFE unit 35 and generates the main image, which is a high-resolution image, in accordance with the pixel information which is read from the pixels in the region S52 of the light receiving unit 28 by the timing generator 34 and the AFE unit 35, under the control of the control unit 555. The display unit 71 displays the main image and the wide-angle image generated by the image processing unit 42.

In the related art, in order to acquire the wide-angle image, an imaging apparatus different from the endoscope apparatus is used or a scope is drawn to the outside in order to check a peripheral region of an operative field. However, according to the fifth embodiment, it is possible to acquire the main image and the wide-angle image, which is an auxiliary image, using only one endoscope at the same time.

Two regions of the light receiving unit 28 set in the first to fifth embodiments make it possible to prevent the following unnecessary operations: an imaging operation is performed during shipping inspection after manufacture; brightness is detected to calculate pixel regions on which light corresponding to each optical system is actually incident; and a read target pixel region is finely adjusted under each control condition to read the pixel on which no light is incident. In addition, even when, for example, the optical system is continuously used and deviates, it is only necessary to electrically set the read target pixel region. Therefore, the position of the optical system may not be adjusted.

In the first to fifth embodiments, the control condition memories 57, 257, 357, 457, and 557 of the control devices 40, 240, 340, 440, and 540 store the control conditions, but the invention is not limited thereto. Each control condition may be stored in a memory (not illustrated) of the CMOS imaging element 80 of the tip portion 5, 205, 305, 405, or 505. In this case, the control units 55, 255, 355, 455, or 555 may notify the control circuit 33 of instruction conditions indicating the control conditions used and the control circuit 33 may select the control conditions indicated by the instruction conditions from the memory (not illustrated) of the CMOS imaging element 80 and control the light receiving unit 28, the timing generator 34, and the AFE unit 35.

Sixth Embodiment

In a sixth embodiment, two optical systems are provided, a right image and a left image are projected onto a light receiving surface of a light receiving unit of a CMOS imaging element at the same time, and the right image and the left image are combined to generate a so-called stereoscopic image.

Figure 33A:
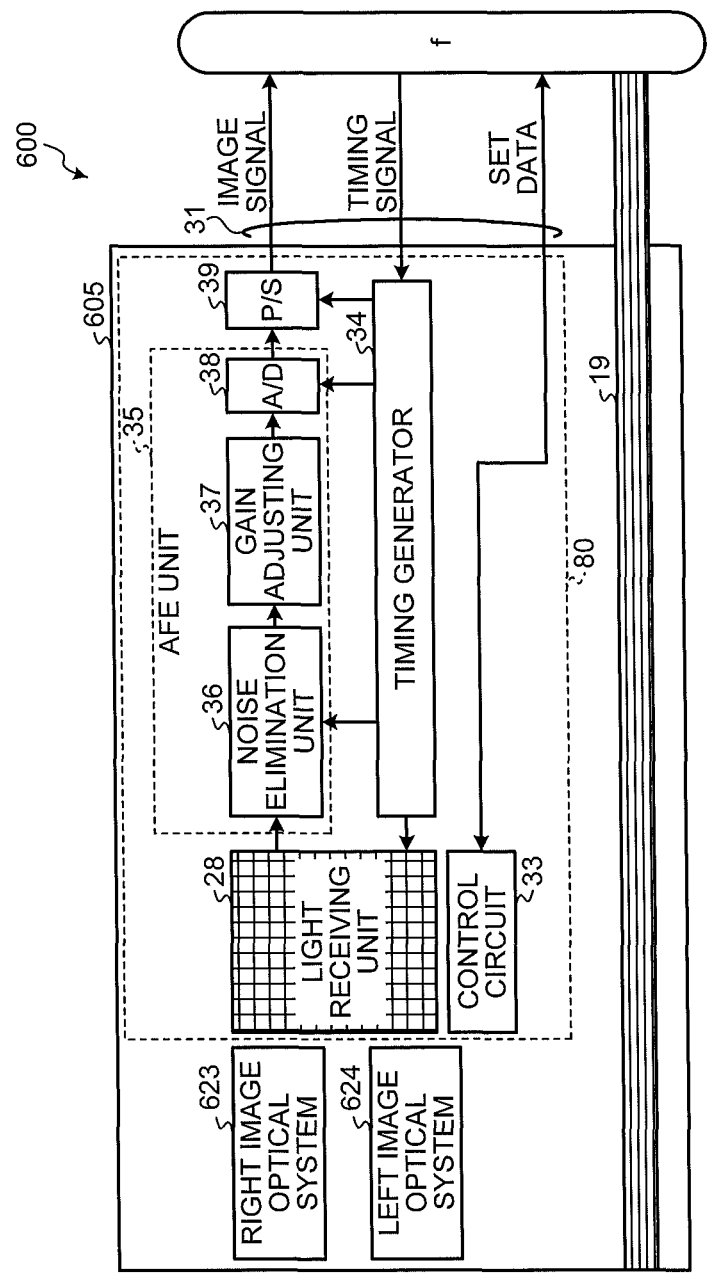
FIGS. 33A and 33B are block diagrams illustrating a structure of an endoscope system according to a sixth embodiment.
Figure 33B:
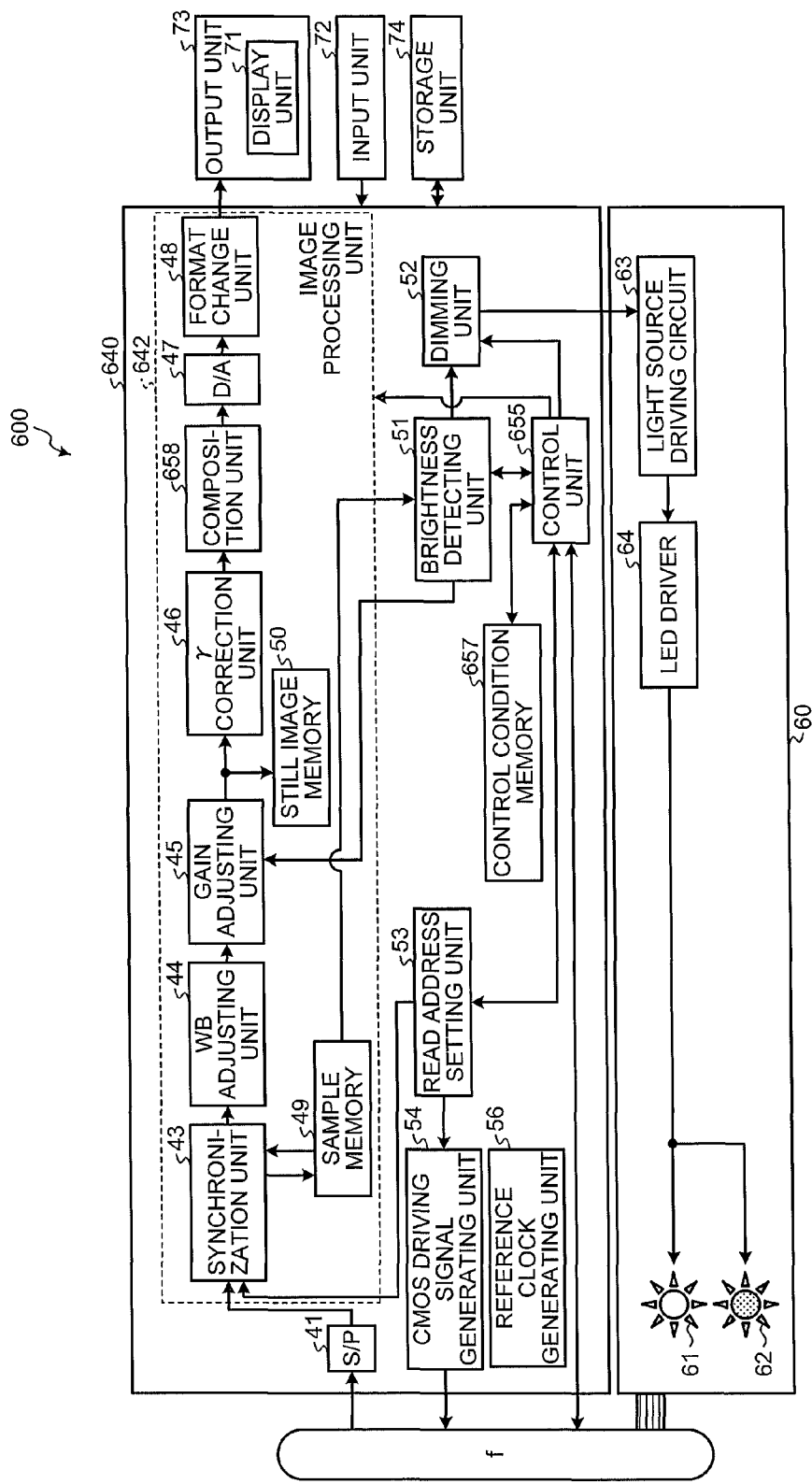

FIGS. 33A and 33B are block diagrams illustrating the structure of an endoscope system according to the sixth embodiment. As illustrated in FIGS. 33A and 33B, in an endoscope system 600 according to the sixth embodiment, a tip portion 605 includes a right image optical system 623 and a left image optical system 624. A control device 640 of the endoscope system 600 includes a control unit 655 having the same function as the control unit 55 instead of the control unit 55 illustrated in FIGS. 6A and 6B and also includes a control condition memory 657 that stores control conditions for forming a so-called stereoscopic image and an image processing unit 642 including a composition unit 658 which combines two images, that is, the right image and the left image acquired at the same time to generate one stereoscopic image.

Figure 34:
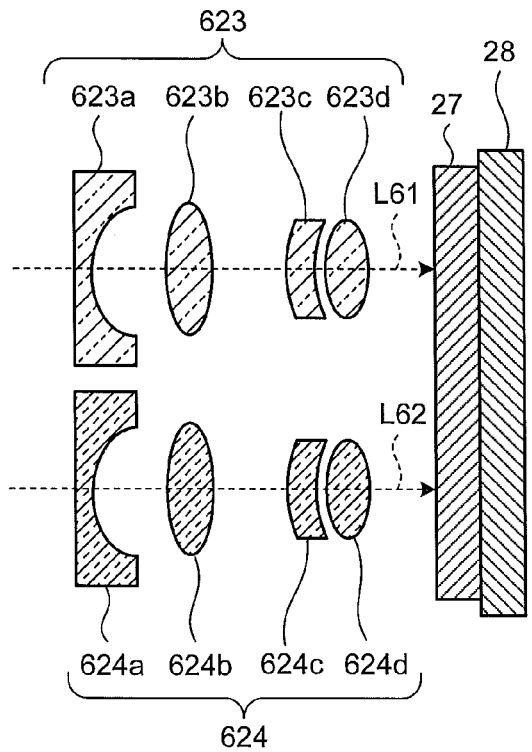
FIG. 34 is a diagram illustrating an example of a right image optical system and a left image optical system illustrated in FIGS. 33A and 33B.
Figure 35:
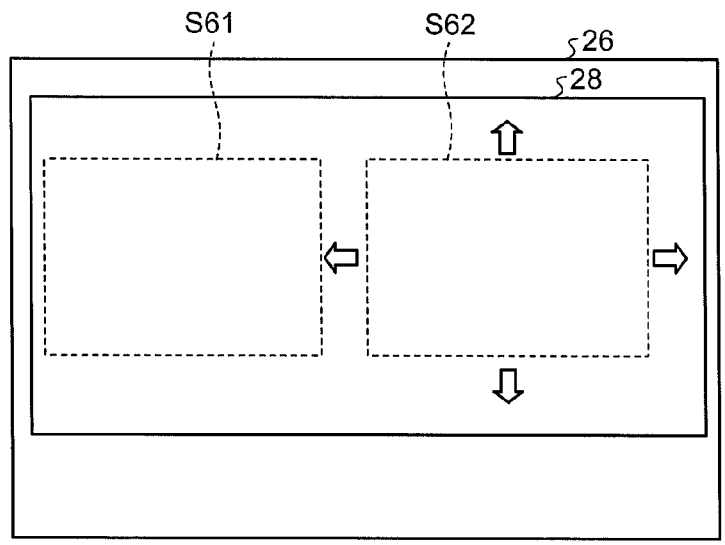
FIG. 35 is a diagram illustrating an example of a light receiving region provided in a light receiving unit illustrated in FIG. 34.

As illustrated in FIG. 34, the right image optical system 623 including lenses 623a to 623d emits light L61 for forming the right image to a right region S61 (see FIG. 35) of the light receiving unit 28. The left image optical system 624 including lenses 624a to 624d emits light L62 for forming the left image to a left region S62 (see FIG. 35) of the light receiving unit. It is preferable that the regions S61 and S62 of the light receiving unit 28 have the same area and shape for a composition process of the composition unit 658.

The control unit 655 directs the read address setting unit 53 to read both pixels in the right region S61 corresponding to the right image optical system 623 and pixels in the left region S62 corresponding to the left image optical system 624 and set the pixels as read target pixels, and directs the timing generator 34 and the AFE unit 35 to read pixel information from the pixels in the right region S61 and the pixels in the left region S62 which are set as the read target pixels by the read address setting unit 53 among a plurality of pixels for imaging in the light receiving unit 28. In the image processing unit 642, the composition unit 658 combines two images, that is, the right image and the left image acquired at the same time to generate one stereoscopic image.

As such, in the sixth embodiment, it is possible to acquire the right image and the left image at the same time with a simple structure including one CMOS imaging element 80 and generate a stereoscopic image. In addition, in the sixth embodiment, as represented by arrows in FIG. 35, for example, the left region S62 is changed in accordance with the right region S61 to position the right image and the left image and adjust parallax in a pseudo manner.

This embodiment is not limited to the endoscope system, but may be applied to imaging apparatuses, such as a digital camera, a digital single reflex camera, a digital video camera, or a mobile phone with a camera. In this case, it is possible to improve efficiency.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging apparatus comprising:
a first optical system that focuses incident light and emits the focused light;
a second optical system that focuses incident light, emits the focused light, and is different from the first optical system in at least one of polarization characteristics and a transparent wavelength;
an imaging unit that includes a light receiving surface divided into a first region on which the light emitted from the first optical system is incident and a second region which is different from the first region and on which the light emitted from the second optical system is incident, can output, as pixel information, an electric signal after photoelectric conversion from pixels which are arbitrarily set as read targets among a plurality of pixels for imaging;
a setting unit that can arbitrarily set pixels as the read targets in the imaging unit and sets the pixels in at least one of the first region and the second region as the read targets;
a reading unit that reads the pixel information from the pixels which are set as the read targets by the setting unit among the plurality of pixels for imaging in the imaging unit;
a control unit that changes the pixels set as the read targets by the setting unit according to an acquisition target image; and
an image processing unit that generates the acquisition target image in accordance with at least one of the pixel information items of the pixels read by the reading unit.

2. The imaging apparatus according to claim 1, wherein the control unit controls a read target pixel setting process of the setting unit, a reading process of the reading unit, and an image generating process of the image processing unit so as to correspond to the acquisition target image.

3. The imaging apparatus according to claim 1, further comprising:
a control condition storage unit that stores control conditions of the control unit so as to correspond to each acquisition target image,
wherein the control unit controls a read target pixel setting process of the setting unit, a reading process of the reading unit, and an image generating process of the image processing unit in accordance with the control condition corresponding to the acquisition target image among the control conditions stored in the control condition storage unit.

4. The imaging apparatus according to claim 1, further comprising:
a display unit that displays an image generated by the image processing unit, wherein
the pixel information includes a brightness value,
the first optical system emits only a component which is polarized along a first polarization plane among the incident light components to the first region of the imaging unit,
the control unit directs the setting unit to set the pixels in the first region and the pixels in the second region as the read targets, directs the reading unit to read the pixel information from the pixels in the first region and the pixels in the second region, to amplify the brightness values of the pixels in the first region at a gain more than that for the brightness values of the pixels in the second region, and to output the brightness values, and directs the image processing unit to generate two images in accordance with the pixel information of the pixels in the first region and the pixel information of the pixels in the second region which are read by the reading unit, and the display unit displays the two images generated by the image processing unit.

5. The imaging apparatus according to claim 4, further comprising:
   a light source; and
   a polarizing unit that emits, to an object, a component which is polarized along a second polarization plane among light components emitted by the light source.

6. The imaging apparatus according to claim 4, wherein the second optical system emits only a component which is polarized along a third polarization plane different from the first polarization plane among the incident light components to the second region of the imaging unit.

7. The imaging apparatus according to claim 1, further comprising:
   a first emission unit that emits a first light component;
   a second emission unit that emits a second light component in a wavelength band wider than that of the first light component, wherein
   the first optical system includes a spectroscopic member that disperses light which is incident from the outside in correspondence with the first light component,
   the control unit directs the first emission unit and the second emission unit to alternately emit light,
   in a first frame in which an image of an object illuminated with the first light component emitted from the first emission unit is captured and the pixel information is output, the control unit directs the setting unit to set the pixels in the first region as the read targets and directs the reading unit to read the pixel information from the pixels in the first region, and
   in a second frame in which an image of the object illuminated with the second light component emitted from the second emission unit is captured and the pixel information is output, the control unit directs the setting unit to set the pixels in the second region as the read targets and directs the reading unit to read the pixel information from the pixels in the second region.

8. The imaging apparatus according to claim 7, wherein the control unit controls an emission process of the first emission unit and the second emission unit and a reading process of the reading unit such that an exposure time in the first frame is more than that in the second frame.

9. The imaging apparatus according to claim 7, wherein the pixel information includes a brightness value, and
   in the first frame, the control unit directs the reading unit to amplify the brightness values of the pixels in the first region at a gain more than that for the brightness values of the pixels in the second region in the second frame and output the amplified brightness values.

10. The imaging apparatus according to claim 7, wherein the pixel information includes a brightness value, and
    the control unit directs the reading unit to add, as the brightness values of the pixels in the first region, the brightness values of a plurality of pixels in a block including a plurality of adjacent pixels and to output the added brightness value in a block unit.

11. The imaging apparatus according to claim 1, further comprising:
    a first emission unit that emits special light in a wavelength band narrower than that of white light; and
    a second emission unit that emits the white light, wherein
    the first optical system includes a first transmission filter that transmits red light and green light among incident light components,
    the second optical system includes a second transmission filter that transmits blue light among incident light components, and
    the control unit controls an emission process of the first emission unit and the second emission unit, a read target pixel setting process of the setting unit, a reading process of the reading unit, and an image generating process of the image processing unit so as to correspond to the acquisition target image.

12. The imaging apparatus according to claim 11, wherein the acquisition target image is an image which is formed by the illumination of the white light, and
    when the acquisition target image is the image which is formed by the illumination of the white light, the control unit directs the second lighting unit to emit the white light, directs the setting unit to set all pixels in the first region and all pixels in the second region as the read targets, directs the reading unit to read the pixel information from all pixels in the first region and all pixels in the second region, and directs the image processing unit to combine an image corresponding to the pixel information of all pixels in the first region and an image corresponding to the pixel information of all pixels in the second region and to generate one image.

13. The imaging apparatus according to claim 11, wherein the acquisition target image is an emphasized image in which a distribution of a specific material is emphasized,
    when the acquisition target image is the emphasized image, the control unit directs the first emission unit to emit, as the special light, light in a wavelength band of green light and blue light, directs the setting unit to set pixels in the first region on which the green light is incident and all pixels in the second region as the read targets, directs the reading unit to read the pixel information from the pixels in the first region on which the green light is incident and all pixels in the second region, and directs the image processing unit to combine an image corresponding to the pixel information of the pixels in the first region on which the green light is incident and an image corresponding to the pixel information of all pixels in the second region and to generate one image.

14. The imaging apparatus according to claim 11, wherein the acquisition target image is a fluorescence observation image, and
    when the acquisition target image is the fluorescence observation image, the control unit directs the first emission unit to emit, as the special light, excitation light for a material which emits fluorescence in a wavelength band of red light and green light, directs the setting unit to set all pixels in the first region as the read targets, directs the reading unit to read the pixel information from all pixels in the first region, and directs the image processing unit to generate one fluorescence observation image in accordance with the pixel information of all pixels in the first region.

15. The imaging apparatus according to claim 14, wherein the control unit directs the setting unit to set all pixels in the first region and all pixels in the second region as the read targets, directs the reading unit to read the pixel information from all pixels in the first region and all pixels in the second region, and directs the image processing unit to generate one monochrome image in accordance with the pixel information of all pixels in the second region.

16. The imaging apparatus according to claim 14, wherein the pixel information includes a brightness value, and
    the control unit directs the setting unit to set all pixels in the first region and all pixels in the second region as the read targets, directs the reading unit to read the pixel information from all pixels in the first region and all pixels in the second region, and directs the image processing unit to correct the brightness values of all pixels in the first region using the brightness values of all pixels in the second region and to generate one fluorescence observation image.

17. The imaging apparatus according to claim 1, wherein
the imaging apparatus is an endoscope apparatus including a tip portion which is inserted into the body, a signal processing device, and a transmission unit which connects the tip portion and the signal processing device,
the tip portion includes the first optical system, the second optical system, the imaging unit, and the reading unit, and
the signal processing device includes the setting unit, the control unit, and the image processing unit.

* * * * *